United States Patent
Leland et al.

(10) Patent No.: US 9,884,096 B2
(45) Date of Patent: *Feb. 6, 2018

(54) COMPOSITIONS AND METHODS RELATED TO GRAFT VERSUS HOST DISEASE AND TREATMENTS THEREOF

(71) Applicant: THE REGENTS OF THE UNIVERSITY OF COLORADO, A BODY, Denver, CO (US)

(72) Inventors: Shapiro Leland, Denver, CO (US); Eli C. Lewis, Be'er Sheva (IL); Charles A. Dinarello, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/266,535

(22) Filed: Apr. 30, 2014

(65) Prior Publication Data

US 2014/0242096 A1 Aug. 28, 2014

Related U.S. Application Data

(63) Continuation of application No. 11/916,521, filed as application No. PCT/US2006/022436 on Jun. 7, 2006, now abandoned, application No. 14/266,535, which is a continuation of application No. 14/063,986, filed on Oct. 25, 2013, now abandoned.

(60) Provisional application No. 60/687,850, filed on Jun. 7, 2005.

(51) Int. Cl.
| | |
|---|---|
| A61K 38/57 | (2006.01) |
| A61K 39/00 | (2006.01) |
| A61K 38/19 | (2006.01) |
| A61K 38/21 | (2006.01) |
| A61K 45/06 | (2006.01) |
| A61K 35/39 | (2015.01) |
| C07K 16/40 | (2006.01) |
| C07K 16/46 | (2006.01) |

(52) U.S. Cl.
CPC .............. *A61K 38/57* (2013.01); *A61K 35/39* (2013.01); *A61K 38/191* (2013.01); *A61K 38/217* (2013.01); *A61K 45/06* (2013.01); *C07K 16/40* (2013.01); *A61K 2039/505* (2013.01)

(58) Field of Classification Search
None
See application file for complete search history.

(56) References Cited

U.S. PATENT DOCUMENTS

| | | |
|---|---|---|
| 4,847,247 A | 7/1989 | Thompson et al. |
| 5,610,285 A | 3/1997 | Lebing et al. |
| 6,022,855 A | 2/2000 | Thomas et al. |
| 6,127,145 A | 10/2000 | Sutliff et al. |
| 6,645,934 B1 | 11/2003 | Rodemann et al. |
| 6,924,267 B2 | 8/2005 | Daemen et al. |
| 7,034,033 B2 | 4/2006 | Boyce et al. |
| 7,304,033 B2 | 12/2007 | Larsen et al. |
| 7,790,685 B2 | 9/2010 | Kiss |
| 2003/0053998 A1 | 3/2003 | Daemen et al. |
| 2003/0105027 A1 | 6/2003 | Rosenbloom |
| 2004/0220242 A1 | 11/2004 | Shapiro |
| 2005/0074848 A1 | 4/2005 | Schwabe |
| 2009/0118162 A1 | 5/2009 | Shapiro et al. |
| 2009/0203580 A1 | 8/2009 | Dinarello et al. |
| 2009/0214467 A1 | 8/2009 | Shakhov et al. |
| 2009/0220518 A1 | 9/2009 | Dinarello et al. |
| 2009/0289182 A1 | 11/2009 | Pevsner |
| 2010/0087436 A1 | 4/2010 | Bardwell et al. |
| 2012/0045449 A1 | 2/2012 | Dinarello et al. |

FOREIGN PATENT DOCUMENTS

| | | |
|---|---|---|
| EP | 0511188 B1 | 6/1997 |
| WO | 0051624 A2 | 9/2000 |
| WO | 02053092 A2 | 7/2002 |
| WO | 2006133403 A2 | 12/2006 |
| WO | 2010088415 A2 | 8/2010 |

OTHER PUBLICATIONS

Korngold et al (Biol. Bld. Marrow Transpl., 2003, 9: 292-303).*
Janciauskiene (Biochem. Biophys. Res. Comm., 2004, 321: 592-600).*
Science Daily (1999, sciencedaily.com/releases/1999/04/990422055930.htm).*
Bitonti et al (PNAS, 2004, 101(26): 9763-9768).*
Zeiser (Hematology Education: the education program for the annual congress of the European Hematology Association, 2014, 8(1): 359-365).*
Soucie and Blazar (Blood, 2009, 114: 4327-4336.*
Barrett and Melenhorst (world wide web at moleculartherapy.org 19(2): 2011).*
OmniBio (2014, Interim Phase 1/2 Data presented at the American Society of Hematology, press release).*
BioSpace (2014, biospace.com).*

(Continued)

*Primary Examiner* — Gerald R Ewoldt
*Assistant Examiner* — Marianne Dibrino
(74) *Attorney, Agent, or Firm* — Faegre Baker Daniels, LLP.

(57) ABSTRACT

Embodiments of the present invention illustrate methods of treating and preventing transplantation and side effects associated with transplantation. In particular, the present invention relates to compositions and methods for inhibition of graft rejection and promotion of graft survival. Thus, the invention relates to modulation of cellular activities, including graft rejection, promotion of graft survival, graft versus host rejection and conditions commonly associated with graft rejection. More particularly, the present invention relates to the inhibitory compounds comprising naturally occurring and man-made inhibitors of serine protease and inducers of other alpha1-antitrypsin activities.

10 Claims, 14 Drawing Sheets

(56) References Cited

OTHER PUBLICATIONS

Marcondes et al (2014, 56th ASH Annual Meeting and Exposition, SanFrancisco, CA, oral and poster abstracts, abstract 3927).*
Kamada (2016, kamada.com/news_item.php?ID=217).*
Marcondes et al (2014, 56th ASH Annual Meeting and Exposition, SanFrancisco, CA, poster).*
Baecher-Allan and Hafler (Immunological Reviews 2006, 212: 203-216).
Barshes et al (J. Leuk. Bioi. 512005, 77: 587-597).
Bell et al. (J. Immumol. 2008, 180: 1508-1516).
Brissova et al (J. Histochem. Cytochem, 2005, 53: 1087).
Chaiet (the Potomac Journal, 2010), Issue 10.
Dong et al.(Ped/Transplant. , 1999, 161 :118-189).
Goodnow, C. (Lancet, 2001, 357: 2115-2121).
International Search Report and Written Opinion of the International Searching Authority, PCT/US08/60848, Dec. 22, 2008.
Kraus and Mayer. (Curr. Opin. Gastroenterol. 2005, 21:692-696).
Lewis et al (PNAS USA Aug. 2005 102: 12153-8, published online before print Aug. 10, 2005).
Lieberman, J., Augmentation therapy reduces frequency of lung infections in antitrypsin deficiency: a new hypothesis with supporting data, Chest, 2000, vol. 118, No. 5, p. 1480-1485.
Lomas, et al., "Preparation and Characterization of Latent alpha-1 antitrypsin." Journal of Biological Chemistry, 270, pp. 5282-5288, Mar. 10, 1995.
Marketletter, Sep. 13, 2009, 2 pages.
O'Riordan et al (Transplantation, 1997, 63(3): 1052-1055).
Panasiuk, A.V., et al., "Disseminated pulmonary tuberculosis, diabetes mellitus and amyloidosis in a patient with hereditary alpha 1-antitrypsin deficiency," Probl Tuberk, 1988, No. 1, p. 72-72.
Pozzilli et al. (Diabetol. 2000,43: 1000-1004).
Rothe et al (J. Immunol. 1999, 163: 1230-1236).
Schroeder et al (J. Surg. Sci. Res. 2003, 111 :109-119).
Skyler et al. (Diabetes Care, 2005, 28:1068-1076).
Song et al (Gene Therapy 2004, 11: 181-186).
Strom (PNAS USA 812005 102: 12153-8, published online before print Aug. 29, 2005).
Yang et al (J. am. Soc. Nephrol. 2003, 14: 214-225).
Couriel et al. A Phase III Study of Infliximab and Corticosteroids fo the Initial Treatment of Acute Graft-Versus-Disease; Biol Blood Marrow Transplant, Dec. 2009, 15(12): pp. 1555-1562.
Hamadani et al. Addition of Infliximab to Standard Acute Graft-Versus-Host Disease Prophylaxis Following Allogeneic Peripheral Blood Cell Transplantation; Biol Blood Marrow Transplant, Jul. 2008; 14(7): pp. 783-789.
Collard et al., "Pathophysiology, Clinical Manifestations, and Prevention of Ischemia-Reperfusion Injury", Anesthesiology, 2001, vol. 94, No. 6, pp. 1133-1138.
de Perrot et al., "Ischemia-Reperfusion-induced Lung Injury" Am J Respir Crit Care Med, 2003, vol. 167, pp. 490-511.
Directive 2004/23/EC of the European Parliament and of the Council of Mar. 31, 2004, cited in Opposition of EP 1 909 810, 11 pages.
Drognitz et al., "Ischemia/Reperfusion Injury Induces Acinar Cell Apoptosis in Experimental Pancreas Transplantation" Transplant Proceed., 2002, vol. 34, p. 2361.
Eltzschig et al., "Vascular ischaemia and reperfusion injury" British Medical Bulletin, 2004, vol. 70, pp. 71-86.
Emamaullee et al., "XIAP Overexpression in Islet β-Cells Enhances Engraftment and Minimizes Hypoxia-Reperfusion Injury", American Journal of Transplantation, 2005, vol. 5, pp. 1297-1305.
Fernandez et al., "Endothelial Keratoplasty: From DLEK to DMEK", Middle East Afr J. Ophtalmol., 2010, vol. 17, No. 1, pp. 5-8.
Fontaine et al., "Islet cell transplantation as a cure for insulin dependent diabetes: current improvements in preserving Islet cell mas and function", HBPD Int., 2003, vol. 2, No. 2, pp. 170-179.
Glazier et al., "Attenuation of reperfusion microvascular ischemia by aqueous oxygen: Experimental and clinical observations", American Heart Journal, 2005, vol. 149, No. 4, pp. 580-584.

Janeway et al., "Reponse to alloantigens and transplant rejection—Immunobiology: The Immune System in Health and Disease", 5th edition, Garland Science, 2001, 9 pages.
Jansson et al., "Graft vascular function after transplantation of pancreatic islets", Diabetologia, 2002, vol. 45, pp. 749-763.
Karow et al., "Organ Preservation for Transplantation", 2nd edition, 1981, Marcel Dekker, Inc., 42 pages.
Keck et al., "Characterization of ischemia/reperfusion injury after pancreas transplantation and reduction by application of monoclonal antibodies against ICAM-1 in the rat", Surgery, Jul. 2003, vol. 134, No. 1, pp. 63-71.
Kupiec-Weglinski et al., "Ischemia and Reperfusion Injury in Liver Transplantation", Transplantation Proceedings, 2005, vol. 37, pp. 1653-1656.
Lin et al., "Hematopoietic Stem Cells Contribute tot he Regeneration of Renal Tubules after Renal Ischemia-Reperfusion Injury in Mice", J Am Soc Nephrol., 2003, vol. 14, pp. 1188-1199.
Mader, Silvia S., "Understanding Human Anatomy & Physiology", 5th edition, The McGraw-Hill Companies, 2004, pp. 2, 84, 85, 170, 196, 197, 210, 256 and 308.
Olsson et al., "Better vascular engraftment and function in pancreatic islets transplanted without prior culture", Diabetologia, 2005, vol. 48, pp. 469-476.
Özmen et al., "Inhibition of Thrombin Abrogates the Instant Blood-Mediated Inflammatory Reaction Triggered by Isolated Human Islets", Diabetes, 2002, vol. 51, pp. 1779-1784.
Paraskevas et al., "Apoptosis Occurs in Freshly Isolated Human Islets Under Standard Culture Conditions", Transpl. Proc., 1997, vol. 29, pp. 750-752.
Pileggi et al., "Factors influencing Islet of Langerhans graft function and monitoring", Clinica Chimica Acta, 2001, vol. 310, pp. 3-16.
Piper et al., "Cellular Mechanisms of Ischemia-Reperfusion Injury" Ann Thorac Surg, 2003, vol. 75, pp. S644-S648.
Ricordi et al., "Automated method for Isolation of Human Pancreatic Islets", Diabetes, 1988, vol. 37, pp. 413-420.
Ryo et al., "Treatment of Post-Transfusion Graft-versus-Host Disease with Nafmostat Mesilate, a Serine Protease Inhibitor", Vox Sang, 1999, vol. 76, pp. 241-246.
Shimmura et al., "Reoxygenation Injury in a Cultured Corneal Epithelial Cell Line Protected by the Uptake of Lactoferrin", Invest Ophtalmol Vis Sci., Jul. 1998, vol. 39, No. 8, pp. 1346-1351.
Skyler, et al., "Use of Inhaled Insulin in a Basal/Bolus Insulin Regimen in Type 1 Diabetic Subjects", Diabetes Care, vol. 28, No. 7, Jul. 2005, pp. 1630-1635.
Song et al., "Experimental Study of Rat Beta Islet Cells Cultured under Simulated Microgravity Conditions", Acta Siochim Biophys Sin, 2004, vol. 36, No. 1, pp. 47-50.
Stratta RJ., "Vascularised pancreas transplantation", BMJ, 1996, vol. 313, pp. 703-704.
Strom, Terry B., "Saving islets from allograft rejection", PNAS, Sep. 6, 2005, vol. 102, No. 36, pp. 12651-12652.
Tögel et al., "Administered mesenchymal stem cells protect against ischemic acute renal failure through differentiation-independent mechanisms", Am. J. physiol. Renal. Physiol., 2005, vol. 289, pp. F31-F42.
Vasir et al., "Effects of diabetes and hypoxia on gene markers of angiogenesis (HGF, cMET, uPA and uPAR, TGF-α, TGF-β, bFGF and Vimentin) in cultured and transplanted rat islets", Diabetologia, 2000, vol. 43, pp. 763-772.
Verma et al., "Fundamentals of Reperfusion Injury for the Clinical Cardiologist", Circulation, 2002, vol. 105, pp. 2332-2336.
Nilkes et al., "Immunobiology of Organ Transplantation", Kluwer Academic/Plenum Publishers 2004, cited in Opposition of EP 1 909 810, 16 pages.
Written Opinion and International Search Report issued by the International Searching Authority for PCT/US2012/050420, dated Feb. 15, 2013, 14 pages.
Yamane et al., "Infliximab for the treatment of severe steroid refractory acute graft-versus-host disease in three patients after allogeneic hematopoietic transplantation", abstract of Leuk Lymphoma, 2003, vol. 44, No. 12, pp. 2095-2097.

(56) References Cited

OTHER PUBLICATIONS

Zhang et al., "Elevated Vascular Endothelial Growth Factor Production in Islets Improves Islet Graft Vascularization", Diabetes, 2004, vol. 53, pp. 963-970.
Andus et al, "Suspected cases of severe side effects after infliximab (Remicade) in Germany", Med Klin (Munich), Aug. 15, 2003, vol. 98, No. 8, pp. 429-436 (Abstract Only).
Anonymous, "Graft-Versus-Host-Disease Clinical Trials", Dana-Farber Cancer Institute, May 2011, www.dana-farber.org/Research/Clinical-Trials-by-Diagnosis.aspx?did=31, 4 pages.
Arora, et al "Alpha-1 Antitrypsin is an Effector of Immunological Stasis", Nature, Aug. 10, 1978, vol. 274, pp. 389-590.
Brantly, et al., "Phase I trial of intramuscular injection of a recombinant adena-associated virus serotype 2 alphal-antitrypsin (AAT) vector in AAT-deficient adults" Human Gene Therapy, Dec. 2006, vol. 17, No. 12, pp. 1177-1186.
Breit, et al., "The role of alpha-antitrypsin deficiency in the pathogenesis of immune disorders", Clinical Immunology and Immunopathology, 1985, vol. 35, pp. 363-380.
Camussi, et al., "Synthesis and Release of Platelet-Activating Factor is Inhibited by Plasma Alpha 1-Proteinase Inhibitor or Alpha 1-Antichymotrypsin and is Stimulated by Proteinases", J. Exp. Med., Oct. 1988, vol. 168, pp. 1293-1306.
Churg, et al., "Alpha-1-Antitrypsin and a Broad Spectrum Metalloprotease Inhibitor, RS113456, Have Similar Acute Anti-Inflammatory Effects", Laboratory Investigation, 2001, vol. 81, No. 8, pp. 1119-1131.
Daemen, et al., "Functional Protection by Acute Phase Proteins a1-Acid Glycoprotein and a1-Antitrypsin Against Ischemia/Reperfusion Injury by Preventing Apoptosis and Inflammation", American Heart Association, 2000, vol. 102, pp. 1420-1426.
Dong, et al., "Transplantation tolerance: The concept and its applicability", Pediatric Transplantation, 1999, vol. 3, pp. 181-192.
Ellerin et al., "Infections and Anti-Tumor Necrosis Factor Therapy", Arthritis & Rheumatism, Nov. 2003, vol. 48, No. 11, pp. 3013-3022.
Extended European Search Report issued in 12823623.9, PCT/US2012/050420, dated Mar. 4, 2015, 9 pages.
Flotte, et al., "Phase I Trial of Intramuscular Injection of a Recombinant Adeno-Associated Virus Alpha 1-Antitrypsin (rAAV2-CB-hAAT) Gene Vector to AAT-Deficient Adults", Human Gene Therapy, 2004, vol. 14, pp. 93-128.
Hagen, et al., "High alpha-1 antitrypsin clearance predicts severity of gut graft-versus-host disease (GVHD) in children", Pediatric Transplantation, 2011, vol. 15, pp. 659-663.
Hill, et al., "Differential roles of IL-1 and TNF-a on graft-versus-host disease and graft versus leukemia", The Journal of Clinical Investigation, Aug. 1999, vol. 104, No. 4, pp. 459-467.
Holler, et al., "Role of Tumor Necrosis Factor Alpha in Acute Graft-Versus-Host Disease and Complications Following Allogenic Bone Marrow Transplantation", Transplant Proceedings, Feb. 1993, vol. 25, No. 1, pp. 1234-1236.
International Search Report and Written Opinion of the International Searching Authority for PCT/US08/60848, dated Dec. 22, 2008, 7 pages.
International Search Report and Written Opinion of the International Searching Authority for PCT/US12/050420, dated Feb. 15, 2013, 7 pages.
International Search Report and Written Opinion of the International Searching Authority for PCT/US2012/028568, dated Jun. 22, 2012, 9 pages.
Janciauskiene, et al., "Immunoregulatory Properties of Acute Phase Proteins—Specific Focus on a1-Antitrypsin, Department of Respiratory Medicine", Hannover Medical School, Hannover, Germany, 2013, Chapter 1, 30 pages.
Ji, et al., "Allogeneic cell-mediated immunotherapy of leukemia with immune donor lymphocytes to upregulate antitumor effects and downregulate antihost responses", Bone Marrow Transplantation, 2003, vol. 32, pp. 495-504.

Keane, et al. "Tuberculosis Associated with Infliximab, a Tumor Necrosis Factor alpha-Neutralizing Agent", New England Journal of Medicine, Oct. 11, 2001, vol. 345, No. 15, pp. 1098-1104.
Kirani, et al., "Co-Existence of Pulmonary Tuberculosis and Diabetes Mellitus: Some Observations", Department of Microbiology, Rangaraya Medical College, Ind J Tub, 1998, vol. 45, pp. 47-48.
Libert, et al., "Alpha 1-Antitrypsin Inhibits the Lethal Response to TNF in Mice", The Journal of Immunology, 1996, vol. 157, No. 11, pp. 5126-5129.
Lomas et al., "Preparation and Characterization of Latent a1-Antitrypsin", The Journal of Biological Chemistry, 1995, vol. 270, No. 10, pp. 5282-5288.
Marcondes, et al., "Inhibition of IL-32 activation by A-1 antitrypsin suppresses alloreactivity and increases survival in an allogeneic murine marrow transplantation model", Blood, Nov. 3, 2011, vol. 118, No. 18, pp. 5031-5039.
Marcondes, et al., Interleukin-32, alpha 1 Anti-Trypsin (AAT-1) and Graft-Versus-Host-Disease, Blood, Nov. 19, 2010, vol. 116 No. 21, 4 pages.
Mohan, et al., "Infectious complications of biologic treatments of rheumatoid arthritis", Current Opinion in Rhuematology, 2003, vol. 15, pp. 179-184.
Mohan, et al. "Tubercluosis following the Use of Etanercept, a Tumor Necrosis Factor Inhibitor", Clinical Infectious Diseases, 2004, vol. 39, pp. 295-299.
Molloy, et al., "Morbidity and mortality in rheumatoid patients during treatment with adalimumab and infliximab", Rheumatology, Letters to the Editor, 2004, vol. 43, No. 4, pp. 522-523.
Notice of Publication issued in PCT/US2006/133403, dated Dec. 14, 2006, 1 page.
Okubo, et al, "Administration of an IL-12-Encoding DNA Plasmid Prevents the Development of Chronic Graft-Versus-Host Disease (GVHD)", The Journal of Immunology, 1999, vol. 162, pp. 4013-4017.
Park, et al., "Identification and Characterization of Human Endometase (Matrix Metalloproteinase-26) from Endometrial Tumor", The Journal of Biological Chemistry, vol. 275, No. 27, Issue of Jul. 7, 2000, pp. 20540-20544, especially p. 20540, col. 2 and p. 20543, col. 2.
Rana, et al., "Radiation-induced biomarkers for the detection and assessment of absorbed radiation doses", Journal of Pharmacy & BioAllied Sciences, 2010, vol. 2, No. 3, pp. 189-196.
Shahaf, et al., "Alpha-1-Antitrypsin Gene Delivery Reduces Inflammation, Increases T-Regulatory Cell Population Size and Prevents Islet Allograft Rejection", Mol Med, 2011, vol. 17, Nos. 9-10, pp. 1000-1011.
Siegel et al. "Safety & Efficacy Update on Approved TNF-Blocking Agents" OTRR, CBER/FDA Arthritis Advisory Committee Mar. 4, 2003, 19 pages.
Tawara, et al., "Alpha-1-antitrypsin monotherapy reduces graft-versus-host disease after experimental allogeneic bone marrow transplantation", Proceedings of the National Academy of Sciences, Jan. 10, 2012, vol. 109, No. 2, pp. 564-569.
Vanhove, et al., "Selective blockade of CD28 and not CTLA-4 with a single-chain Fv-alpha1-antitrypsin fusion antibody", Blood, Jul. 15, 2003, vol. 102, No. 2, pp. 564-570.
Vidal, et al., "Severe neutropenia and thrombocytopenia associated with infliximab", Ann Intern. Med, Aug. 5, 2003, vol. 139, No. 3, pp. W-W63. (Abstract only).
Wallis, et al., "Reactivation of Latent Granulomatous Infections by Infliximab", Clinical Infectious Diseases, 2005, vol. 41, pp. S194-S198.
Warris, et al., "Invasive Pulmonary Aspergillosis Associated with Infliximab Therapy", New England Journal of Medicine, Apr. 5, 2001, vol. 344, No. 14, pp. 1099-1100.
Wolfe, et al., "The Effect of Methotrexate and Anti-Tumor Necrosis Factor Therapy in 18,572 Patients", Arthritis & Rheumatism, Jun. 2004, vol. 50, No. 6, pp. 1740-1751.
Abstract of US/2012/0045449 A1, Dinarello,et al., Feb. 23, 2012, 1 page.
Arita, et al., "Islet Graft Primary Nonfunction and Its Prevention", Transplant Proceedings, 200, vol. 32, p. 1667.

(56) References Cited

OTHER PUBLICATIONS

Arumugam, et al., "The role of the complement system in ischemia-reperfusion injury", Shock, 2004, vol. 21, No. 5, pp. 401-409.
Boyle, et al., "Ischemia-Reperfusion Injury", Ann Thorac Surg, 1997, vol. 64, pp. S24-S30.
Bulkley G. B., "Free radical-mediated reperfusion injury: A selective review", Br. J. Cancer., 1987, vol. 55, pp. 66-S73.
Carlsson, et al., "Engraftment and Growth of Transplanted Pancreatic Islets", Upsala J Med Sc., 2000, vol. 105, No. 2, pp. 107-123.
Carlsson, et al., "Low Revascularization of Experimentally Transplanted Human Pancreatic Islets", J. Clin. Endocrinol. Metab., 2002, Vo. 87, No. 12, pp. 5418-5423.
Carlsson, et al., "Markedly Decreased Oxygen Tension in Transplanted Rat Pancreatic Islets Irrespective of the Implantation Site", Diabetes, Mar. 2001, vol. 50, pp. 489-495.
Herodin et al., Radioprotective Effect of an Acute Non-specific Inflammation in Mice. International Journal of Radiation Biology. Mar. 1987, vol. 51, No. 3, pp. 549-559; Note: A copy of this article was unretrievable. The abstract has been included.
Wikipedia. List of Organs of the Human Body. (Modified Jul. 15, 2015). Retrieved Aug. 19, 2015 from: wikipedia.org/wiki/List_of_organs_of_the_human_body.
Wikipedia. Organ (anatomy). (Modified Aug. 12, 2015). Retrieved Aug. 19, 2015 en.wikipedia.org/wiki/Organ_(anatomy).

* cited by examiner

CD4
(Lymphocytes)

CD11b
(Monocytes/PMN)

SEQUENCE LISTING

<160> NUMBER OF SEQ ID NOS: 65

<210> SEQ ID NO 1
<211> LENGTH: 5
<212> TYPE: PRT
<213> ORGANISM: Artificial

-continued

```
<220> FEATURE:
<223> OTHER INFORMATION: synthetic peptide

<400> SEQUENCE: 1

Phe Val Phe Leu Met
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Phe Val Phe Ala Met
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Phe Val Ala Leu Met
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Phe Val Phe Leu Ala
1               5

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Phe Leu Val Phe Ile
1               5

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Phe Leu Met Ile Ile
1               5

<210> SEQ ID NO 7
<211> LENGTH: 5
<212> TYPE: PRT
<213> ORGANISM: Artificial
<220> FEATURE:
```

```
<223> OTHER INFORMATION: synthetic peptide

<400> SEQUENCE: 7

Phe Leu Phe Val Leu
1               5

<210> SEQ ID NO 8
<211> LENGTH: 5
<212> TYPE: PRT
<213> ORGANISM: Artificial
<220> FEATURE:
<223> OTHER INFORMATION: synthetic peptide

<400> SEQUENCE: 8

Phe Leu Phe Val Val
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Phe Leu Phe Leu Ile
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Leu Phe Phe Ile
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Phe Leu Met Phe Ile
1               5

<210> SEQ ID NO 12
<211> LENGTH: 5
<212> TYPE: PRT
<213> ORGANISM: Artificial
<220> FEATURE:
<223> OTHER INFORMATION: synthetic peptide

<400> SEQUENCE: 12

Phe Met Leu Leu Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide
```

```
<400> SEQUENCE: 13

Phe Ile Ile Met Ile
1               5

<210> SEQ ID NO 14
<211> LENGTH: 5
<212> TYPE: PRT
<213> ORGANISM: Artificial
<220> FEATURE:
<223> OTHER INFORMATION: synthetic peptide

<400> SEQUENCE: 14

Phe Leu Phe Cys Ile
1               5

<210> SEQ ID NO 15
<211> LENGTH: 5
<212> TYPE: PRT
<213> ORGANISM: Artificial
<220> FEATURE:
<223> OTHER INFORMATION: synthetic peptide

<400> SEQUENCE: 15

Phe Leu Phe Ala Val
1               5

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Phe Val Tyr Leu Ile
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Phe Ala Phe Leu Met
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

<400> SEQUENCE: 18

Ala Val Phe Leu Met
1               5

<210> SEQ ID NO 19
<211> LENGTH: 10
<212> TYPE: PRT
<213> ORGANISM: Homo sapiens

<400> SEQUENCE: 19
```

```
Met Pro Ser Ser Val Ser Trp Gly Ile Leu
1               5                   10

<210> SEQ ID NO 20
<211> LENGTH: 10
<212> TYPE: PRT
<213> ORGANISM: Homo sapiens

<400> SEQUENCE: 20

Leu Ala Gly Leu Cys Cys Leu Val Pro Val
1               5                   10

<210> SEQ ID NO 21
<211> LENGTH: 10
<212> TYPE: PRT
<213> ORGANISM: Homo sapiens

<400> SEQUENCE: 21

Ser Leu Ala Glu Asp Pro Gln Gly Asp Ala
1               5                   10

<210> SEQ ID NO 22
<211> LENGTH: 10
<212> TYPE: PRT
<213> ORGANISM: Homo sapiens

<400> SEQUENCE: 22

Ala Gln Lys Thr Asp Thr Ser His His Asp
1               5                   10

<210> SEQ ID NO 23
<211> LENGTH: 10
<212> TYPE: PRT
<213> ORGANISM: Homo sapiens

<400> SEQUENCE: 23

Gln Asp His Pro Thr Phe Asn Lys Ile Thr
1               5                   10

<210> SEQ ID NO 24
<211> LENGTH: 10
<212> TYPE: PRT
<213> ORGANISM: Homo sapiens

<400> SEQUENCE: 24

Pro Asn Leu Ala Glu Phe Ala Phe Ser Leu
1               5                   10

<210> SEQ ID NO 25
<211> LENGTH: 10
<212> TYPE: PRT
<213> ORGANISM: Homo sapiens

<400> SEQUENCE: 25

Tyr Arg Gln Leu Ala His Gln Ser Asn Ser
1               5                   10

<210> SEQ ID NO 26
<211> LENGTH: 10
<212> TYPE: PRT
<213> ORGANISM: Homo sapiens

<400> SEQUENCE: 26

Thr Asn Ile Phe Phe Ser Pro Val Ser Ile
1               5                   10
```

```
<210> SEQ ID NO 27
<211> LENGTH: 10
<212> TYPE: PRT
<213> ORGANISM: Homo sapiens

<400> SEQUENCE: 27

Ala Thr Ala Phe Ala Met Leu Ser Leu Gly
1               5                   10

<210> SEQ ID NO 28
<211> LENGTH: 10
<212> TYPE: PRT
<213> ORGANISM: Homo sapiens

<400> SEQUENCE: 28

Thr Lys Ala Asp Thr His Asp Glu Ile Leu
1               5                   10

<210> SEQ ID NO 29
<211> LENGTH: 10
<212> TYPE: PRT
<213> ORGANISM: Homo sapiens

<400> SEQUENCE: 29

Glu Gly Leu Asn Phe Asn Leu Thr Glu Ile
1               5                   10

<210> SEQ ID NO 30
<211> LENGTH: 10
<212> TYPE: PRT
<213> ORGANISM: Homo sapiens

<400> SEQUENCE: 30

Pro Glu Ala Gln Ile His Glu Gly Phe Gln
1               5                   10

<210> SEQ ID NO 31
<211> LENGTH: 10
<212> TYPE: PRT
<213> ORGANISM: Homo sapiens

<400> SEQUENCE: 31

Glu Leu Leu Arg Thr Leu Asn Gln Pro Asp
1               5                   10

<210> SEQ ID NO 32
<211> LENGTH: 10
<212> TYPE: PRT
<213> ORGANISM: Homo sapiens

<400> SEQUENCE: 32

Ser Gln Leu Gln Leu Thr Thr Gly Asn Gly
1               5                   10

<210> SEQ ID NO 33
<211> LENGTH: 10
<212> TYPE: PRT
<213> ORGANISM: Homo sapiens

<400> SEQUENCE: 33

Leu Phe Leu Ser Glu Gly Leu Lys Leu Val
1               5                   10
```

```
<210> SEQ ID NO 34
<211> LENGTH: 10
<212> TYPE: PRT
<213> ORGANISM: Homo sapiens

<400> SEQUENCE: 34

Asp Lys Phe Leu Glu Asp Val Lys Lys Leu
1               5                   10

<210> SEQ ID NO 35
<211> LENGTH: 10
<212> TYPE: PRT
<213> ORGANISM: Homo sapiens

<400> SEQUENCE: 35

Tyr His Ser Glu Ala Phe Thr Val Asn Phe
1               5                   10

<210> SEQ ID NO 36
<211> LENGTH: 10
<212> TYPE: PRT
<213> ORGANISM: Homo sapiens

<400> SEQUENCE: 36

Gly Asp His Glu Glu Ala Lys Lys Gln Ile
1               5                   10

<210> SEQ ID NO 37
<211> LENGTH: 10
<212> TYPE: PRT
<213> ORGANISM: Homo sapiens

<400> SEQUENCE: 37

Asn Asp Tyr Val Glu Lys Gly Thr Gln Gly
1               5                   10

<210> SEQ ID NO 38
<211> LENGTH: 10
<212> TYPE: PRT
<213> ORGANISM: Homo sapiens

<400> SEQUENCE: 38

Lys Ile Val Asp Leu Val Lys Glu Leu Asp
1               5                   10

<210> SEQ ID NO 39
<211> LENGTH: 10
<212> TYPE: PRT
<213> ORGANISM: Homo sapiens

<400> SEQUENCE: 39

Arg Asp Thr Val Phe Ala Leu Val Asn Tyr
1               5                   10

<210> SEQ ID NO 40
<211> LENGTH: 10
<212> TYPE: PRT
<213> ORGANISM: Homo sapiens

<400> SEQUENCE: 40

Ile Phe Phe Lys Gly Lys Trp Glu Arg Pro
1               5                   10

<210> SEQ ID NO 41
<211> LENGTH: 10
```

-continued

<212> TYPE: PRT
<213> ORGANISM: Homo sapiens

<400> SEQUENCE: 41

Phe Glu Val Lys Asp Thr Glu Asp Glu Asp
1               5                   10

<210> SEQ ID NO 42
<211> LENGTH: 10
<212> TYPE: PRT
<213> ORGANISM: Homo sapiens

<400> SEQUENCE: 42

Phe His Val Asp Gln Val Thr Thr Val Lys
1               5                   10

<210> SEQ ID NO 43
<211> LENGTH: 10
<212> TYPE: PRT
<213> ORGANISM: Homo sapiens

<400> SEQUENCE: 43

Val Pro Met Met Lys Arg Leu Gly Met Phe
1               5                   10

<210> SEQ ID NO 44
<211> LENGTH: 10
<212> TYPE: PRT
<213> ORGANISM: Homo sapiens

<400> SEQUENCE: 44

Asn Ile Gln His Cys Lys Lys Leu Ser Ser
1               5                   10

<210> SEQ ID NO 45
<211> LENGTH: 10
<212> TYPE: PRT
<213> ORGANISM: Homo sapiens

<400> SEQUENCE: 45

Trp Val Leu Leu Met Lys Tyr Leu Gly Asn
1               5                   10

<210> SEQ ID NO 46
<211> LENGTH: 10
<212> TYPE: PRT
<213> ORGANISM: Homo sapiens

<400> SEQUENCE: 46

Ala Thr Ala Ile Phe Phe Leu Pro Asp Glu
1               5                   10

<210> SEQ ID NO 47
<211> LENGTH: 10
<212> TYPE: PRT
<213> ORGANISM: Homo sapiens

<400> SEQUENCE: 47

Gly Lys Leu Gln His Leu Glu Asn Glu Leu
1               5                   10

<210> SEQ ID NO 48
<211> LENGTH: 10
<212> TYPE: PRT
<213> ORGANISM: Homo sapiens -continued

```
<400> SEQUENCE: 48

Thr His Asp Ile Ile Thr Lys Phe Leu Glu
1               5                   10

<210> SEQ ID NO 49
<211> LENGTH: 10
<212> TYPE: PRT
<213> ORGANISM: Homo sapiens

<400> SEQUENCE: 49

Asn Glu Asp Arg Arg Ser Ala Ser Leu His
1               5                   10

<210> SEQ ID NO 50
<211> LENGTH: 10
<212> TYPE: PRT
<213> ORGANISM: Homo sapiens

<400> SEQUENCE: 50

Leu Pro Lys Leu Ser Ile Thr Gly Thr Tyr
1               5                   10

<210> SEQ ID NO 51
<211> LENGTH: 10
<212> TYPE: PRT
<213> ORGANISM: Homo sapiens

<400> SEQUENCE: 51

Asp Leu Lys Ser Val Leu Gly Gln Leu Gly
1               5                   10

<210> SEQ ID NO 52
<211> LENGTH: 10
<212> TYPE: PRT
<213> ORGANISM: Homo sapiens

<400> SEQUENCE: 52

Ile Thr Lys Val Phe Ser Asn Gly Ala Asp
1               5                   10

<210> SEQ ID NO 53
<211> LENGTH: 10
<212> TYPE: PRT
<213> ORGANISM: Homo sapiens

<400> SEQUENCE: 53

Leu Ser Gly Val Thr Glu Glu Ala Pro Leu
1               5                   10

<210> SEQ ID NO 54
<211> LENGTH: 10
<212> TYPE: PRT
<213> ORGANISM: Homo sapiens

<400> SEQUENCE: 54

Lys Leu Ser Lys Ala Val His Lys Ala Val
1               5                   10

<210> SEQ ID NO 55
<211> LENGTH: 10
<212> TYPE: PRT
<213> ORGANISM: Homo sapiens

<400> SEQUENCE: 55
```

```
Leu Thr Ile Asp Glu Lys Gly Thr Glu Ala
1               5                   10

<210> SEQ ID NO 56
<211> LENGTH: 10
<212> TYPE: PRT
<213> ORGANISM: Homo sapiens

<400> SEQUENCE: 56

Ala Gly Ala Met Phe Leu Glu Ala Ile Pro
1               5                   10

<210> SEQ ID NO 57
<211> LENGTH: 10
<212> TYPE: PRT
<213> ORGANISM: Homo sapiens

<400> SEQUENCE: 57

Met Ser Ile Pro Pro Glu Val Lys Phe Asn
1               5                   10

<210> SEQ ID NO 58
<211> LENGTH: 10
<212> TYPE: PRT
<213> ORGANISM: Homo sapiens

<400> SEQUENCE: 58

Lys Pro Phe Val Phe Leu Met Ile Glu Gln
1               5                   10

<210> SEQ ID NO 59
<211> LENGTH: 10
<212> TYPE: PRT
<213> ORGANISM: Homo sapiens

<400> SEQUENCE: 59

Asn Thr Lys Ser Pro Leu Phe Met Gly Lys
1               5                   10

<210> SEQ ID NO 60
<211> LENGTH: 7
<212> TYPE: PRT
<213> ORGANISM: Homo sapiens

<400> SEQUENCE: 60

Val Val Asn Pro Thr Gln Lys
1               5

<210> SEQ ID NO 61
<211> LENGTH: 417
<212> TYPE: PRT
<213> ORGANISM: Homo sapiens

<400> SEQUENCE: 61

Met Pro Ser Ser Val Ser Trp Gly Ile Leu Leu Ala Gly Leu Cys Cys
1               5                   10                  15

Leu Val Pro Val Ser Leu Ala Glu Asp Pro Gln Gly Asp Ala Ala Gln
            20                  25                  30

Lys Thr Asp Thr Ser His His Asp Gln Asp His Pro Thr Phe Asn Lys
        35                  40                  45

Ile Thr Pro Asn Leu Ala Glu Phe Ala Phe Ser Leu Tyr Arg Gln Leu
    50                  55                  60
```

```
Ala His Gln Ser Asn Ser Thr Asn Ile Phe Phe Ser Pro Val Ser Ile
 65                  70                  75                  80

Ala Thr Ala Phe Ala Met Leu Ser Leu Gly Thr Lys Ala Asp Thr His
                 85                  90                  95

Asp Glu Ile Leu Glu Gly Leu Asn Phe Asn Leu Thr Glu Ile Pro Glu
            100                 105                 110

Ala Gln Ile His Glu Gly Phe Gln Glu Leu Leu Arg Thr Leu Asn Gln
            115                 120                 125

Pro Asp Ser Gln Leu Gln Thr Thr Gly Asn Gly Leu Phe Leu Ser
130                 135                 140

Glu Gly Leu Lys Leu Val Asp Lys Phe Leu Glu Asp Val Lys Lys Leu
145                 150                 155                 160

Tyr His Ser Glu Ala Phe Thr Val Asn Phe Gly Asp His Glu Glu Ala
                165                 170                 175

Lys Lys Gln Ile Asn Asp Tyr Val Glu Lys Gly Thr Gln Gly Lys Ile
            180                 185                 190

Val Asp Leu Val Lys Glu Leu Asp Arg Asp Thr Val Phe Ala Leu Val
            195                 200                 205

Asn Tyr Ile Phe Phe Lys Gly Lys Trp Glu Arg Pro Phe Glu Val Lys
210                 215                 220

Asp Thr Glu Asp Glu Asp Phe His Val Asp Gln Val Thr Thr Val Lys
225                 230                 235                 240

Val Pro Met Met Lys Arg Leu Gly Met Phe Asn Ile Gln His Cys Lys
                245                 250                 255

Lys Leu Ser Ser Trp Val Leu Leu Met Lys Tyr Leu Gly Asn Ala Thr
            260                 265                 270

Ala Ile Phe Phe Leu Pro Asp Glu Gly Lys Leu Gln His Leu Glu Asn
            275                 280                 285

Glu Leu Thr His Asp Ile Ile Thr Lys Phe Leu Glu Asn Glu Asp Arg
290                 295                 300

Arg Ser Ala Ser Leu His Leu Pro Lys Leu Ser Ile Thr Gly Thr Tyr
305                 310                 315                 320

Asp Leu Lys Ser Val Leu Gly Gln Leu Gly Ile Thr Lys Val Phe Ser
                325                 330                 335

Asn Gly Ala Asp Leu Ser Gly Val Thr Glu Glu Ala Pro Leu Lys Leu
            340                 345                 350

Ser Lys Ala Val His Lys Ala Val Leu Thr Ile Asp Glu Lys Gly Thr
            355                 360                 365

Glu Ala Ala Gly Ala Met Phe Leu Glu Ala Ile Pro Met Ser Ile Pro
370                 375                 380

Pro Glu Val Lys Phe Asn Lys Pro Phe Val Phe Leu Met Ile Glu Gln
385                 390                 395                 400

Asn Thr Lys Ser Pro Leu Phe Met Gly Lys Val Val Asn Pro Thr Gln
                405                 410                 415

Lys

<210> SEQ ID NO 62
<211> LENGTH: 394
<212> TYPE: PRT
<213> ORGANISM: Homo sapiens

<400> SEQUENCE: 62

Glu Asp Pro Gln Gly Asp Ala Ala Gln Lys Thr Asp Thr Ser His His
 1                   5                  10                  15
```

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
        130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 63
<211> LENGTH: 5
<212> TYPE: PRT
<213> ORGANISM: Artificial
<220> FEATURE:
<223> OTHER INFORMATION: synthetic peptide

```
<400> SEQUENCE: 63

Phe Val Phe Leu Met
1               5

<210> SEQ ID NO 64
<211> LENGTH: 5
<212> TYPE: PRT
<213> ORGANISM: Artificial
<220> FEATURE:
<223> OTHER INFORMATION: synthetic peptide

<400> SEQUENCE: 64

Phe Val Phe Ala Met
1               5

<210> SEQ ID NO 65
<211> LENGTH: 5
<212> TYPE: PRT
<213> ORGANISM: Artificial
<220> FEATURE:
<223> OTHER INFORMATION: synthetic peptide

<400> SEQUENCE: 65

Phe Val Ala Leu Met
1               5
```

COMPOSITIONS AND METHODS RELATED TO GRAFT VERSUS HOST DISEASE AND TREATMENTS THEREOF

PRIORITY

This application is a continuation of U.S. application Ser. No. 14/063,986 filed Oct. 25, 2013 and U.S. application Ser. No. 11/916,521 filed Dec. 4, 2007, which is a national stage application of PCT Application No. PCT/US2006/22436, filed Jun. 7, 2006, which claims priority to U.S. Provisional Application No. 60/687,580 filed Jun. 7, 2005. All prior applications are incorporated herein in their entirety by reference for all purposes.

FIELD

Embodiments of the present invention relate to compositions and methods for treatment of subjects in need of or having a transplant. In particular, embodiments of the present invention relate to compositions and methods for treatment of conditions associated with transplantations in a subject, for example, graft rejection. More particularly, the present invention relates to compositions and uses of alpha1-antitrypsin ($\alpha$1-antitrypsin) and agents with $\alpha$-antitrypsin-like activity and/or compositions and uses of serine protease inhibitors.

BACKGROUND

Serine Proteases

Serine proteases serve an important role in human physiology by mediating the activation of vital functions. In addition to their normal physiological function, serine proteases have been implicated in a number of pathological conditions in humans. Serine proteases are characterized by a catalytic triad consisting of aspartic acid, histidine and serine at the active site.

Naturally occurring serine protease inhibitors have been classified into families primarily on the basis of the disulfide bonding pattern and the sequence homology of the reactive site. Serine protease inhibitors, including the group known as serpins, have been found in microbes, in the tissues and fluids of plants, animals, insects and other organisms. At least nine separate, well-characterized proteins are now identified, which share the ability to inhibit the activity of various proteases. Several of the inhibitors have been grouped together, namely $\alpha$1-antitrypsin-proteinase inhibitor, secretory leukocyte protease inhibitor or SLPI, anti-thrombin III, antichymotrypsin, C1-inhibitor, and $\alpha$2-antiplasmin, which are directed against various serine proteases, i.e., leukocyte elastase, thrombin, cathepsin G, chymotrypsin, plasminogen activators, and plasmin. These inhibitors are members of the $\alpha$1-antitrypsin-proteinase inhibitor class. The protein $\alpha$2-macroglobulin inhibits members of all four classes of endogenous proteases: serine, cysteine, aspartic, and metalloproteases. However, other types of protease inhibitors are class specific. For example, the $\alpha$1-antitrypsin-proteinase inhibitor (also known as $\alpha$1-antitrypsin or AAT) and inter-alpha-trypsin inhibitor inhibit only serine proteases, $\alpha$1-cysteine protease inhibitor inhibits cysteine proteases, and $\alpha$1-anticollagenase inhibits collagenolytic enzymes of the metalloenzyme class.

The normal plasma concentration of AAT ranges from 1.3 to 3.5 mg/ml although it can behave as an acute phase reactant and increase 3-4-fold during host response to inflammation and/or tissue injury such as with pregnancy, acute infection, and tumors. It easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen. AAT appears to represent an important part of the defense mechanism against activity by serine proteases.

$\alpha$1-antitrypsin is one of few naturally occurring mammalian serine protease inhibitors currently approved for the clinical therapy of protease imbalance. Therapeutic $\alpha$1-antitrypsin has been commercially available since the mid 1980's and is prepared by various purification methods (see for example Bollen et al., U.S. Pat. No. 4,629,567; Thompson et al., U.S. Pat. Nos. 4,760,130; 5,616,693; WO 98/56821). Prolastin is a trademark for a purified variant of $\alpha$1-antitrypsin and is currently sold by Talecris Company (U.S. Pat. No. 5,610,285 Lebing et al., Mar. 11, 1997). Recombinant unmodified and mutant variants of $\alpha$1-antitrypsin produced by genetic engineering methods are also known (U.S. Pat. No. 4,711,848); methods of use are also known, e.g., ($\alpha$1-antitrypsin gene therapy/delivery) (U.S. Pat. No. 5,399,346).

Graft Rejection

There are many diseases that culminate in organ dysfunction or failure. Representative non-limiting examples include renal failure due to diabetes mellitus, hypertension, urinary output obstruction, drug-induced toxicity, or hypoperfusion, as well as cardiac dysfunction due to ischemic coronary artery disease, cardiomyopathy/infection, or valvulopathy. Pulmonary diseases include substantial damage due to chronic obstructive pulmonary disease (COPD, including chronic bronchitis and emphysema), AAT deficiency, cystic fibrosis, and interstitial fibrosis. Under certain conditions, the only therapeutic option for treatment of a subject may be organ transplantation. Pancreatic-islet transplantation provides diabetic patients with the only option for a tightly-controlled blood glucose level, as proven to be essential for prevention of diabetic complications. In the case of islets, post-transplant inflammation, which precedes immune rejection, is a critical determinant of graft survival. This early inflammation is mediated by cells other than the impending allospecific immune cells.

One challenge to therapeutic transplantation is the damaging effects of the host immune system on the transplant. MHC molecules exist on the surfaces of cells and the particular structures of MHC molecules are typically unique for each individual (with the exception of identical twins, where the MHC molecule complements are identical). The immune system is programmed to attack foreign or "non-self" MHC-bearing tissues. For these reasons, when an organ or tissue is transplanted into a recipient, an effort is made to optimize the degree of tissue matching between donor and recipient. MHC antigens are characterized for the recipient and donors. Matching a donor to an allograft recipient by MHC structure reduces the magnitude of the rejection response. An archetypal example is blood group matching. Most transplants are allografts that occur between non-identical members of the same species. Since these matches are imperfect, there is an expected graft rejection immune response associated with allografts. Current methods used, in order to enhance graft survival, include medications to suppress the immune response which can result in graft rejection. These medications are referred to immunosuppressant or antirejection drugs, such as prednisone, cyclosporine A, and cyclophosphamide, to name a few. As mentioned above, local inflammation is experienced immediately after grafting, and cells that are particularly sensitive to non-specific inflammation, such as islets, can endure graft dysfunction more severely than other types.

Despite advances in the field of antirejection therapy, graft maintenance remains a challenge since the available antirejection therapies are imperfect. For example, immunosuppression enhances the risk for opportunistic infection or neoplasia. Toxicities abound and include, but are not limited to, diabetes, organ dysfunction, renal failure, hepatic dysfunction, hematological defects, neuromuscular and psychiatric side effects, and many others. Therefore, there is a need for a more effective anti-rejection medical treatment that prolong graft survival and improve the quality of life.

Bone marrow transplantation is a unique kind of transplant where immune cells from a donor are transferred into a recipient, thereby conferring the donor immune system into the recipient. Here, the graft is capable of generating an immune response against the host, and this is termed "graft versus host" disease (GVHD). Immunosuppressive and antimicrobial treatment is required to block adverse consequences of GVHD, and a need exists for safer and more effective inhibitors of the adverse effects by the graft.

Because of some of the difficulties and inadequacies of conventional therapy for treating transplantation complications and associated side-effects, new therapeutic modalities are needed.

SUMMARY

Embodiments of the present invention provide for methods for treating a subject having or in need of a transplant. In accordance with these embodiments, a subject may be treated with a composition for reducing the risk of a transplant rejection or a side-effect of a transplant rejection in a subject. In accordance with this method, the subject can be administered a composition including a compound that is capable of significantly reducing serine protease activity. The composition may be administered before transplantation, during transplantation, after transplantation or combination thereof. In addition, the composition may further include one or more anti-transplant rejection agent, anti-inflammatory agent, immunosuppressive agent, immunomodulatory agent, anti-microbial agent, or a combination thereof.

In certain embodiments of the invention, a composition capable of significantly reducing serine protease activity can include alpha-1-antitrypsin, an analog thereof or a combination thereof. A transplant of the present invention may include an organ transplant and/or a non-organ transplant. For example lung, kidney, heart, liver, cornea, skin, stem cells, soft tissue (e.g. facial component transplant), intestinal transplants, bone marrow, pancreatic islet, pancreas transplant or combination thereof are contemplated.

Embodiments of the present invention provide for methods for ameliorating symptoms or signs experienced by a subject having or in need of a transplant. In accordance with these embodiments, symptoms or signs may include conditions associated with graft versus host disease (GVHD), or graft rejection. In one example, methods disclosed herein may be used to treat a subject undergoing bone marrow transplantation. In another embodiment, symptoms or signs may include, but is not limited to, one or more of the following, kidney failure, lung failure, heart failure, malaise, fever, dry cough, anorexia, weight loss, myalgias, and chest pains, ventilatory compromise, sweating, nausea, vomiting, fever, abdominal pain, bloody diarrhea, mucosal ulcerations, reduced renal function (increased creatinine, decreased urine output), reduced pulmonary function (increased shortness of breath, fever, cough, sputum, hypoxemia), reduced cardiac function (shortness of breath, chest pain, fatigue, pulmonary or peripheral edema, valvulopathy), reduced islet function (increased glucose, diabetes mellitus), graft versus host disease (gastrointestinal (GI) ulceration, pulmonary failure, skin ulceration, coagulopothy, CNS dysfunction (mental status changes, coma) CMV (cytomegalovirus infection, viral, fungal parasitic infection)).

Embodiments of the present invention provide methods for promoting prolonged graft survival and function in a subject including administering to a subject in need thereof a therapeutically effective amount of a composition including a substance exhibiting $\alpha$1-antitrypsin or $\alpha$1-antitrypsin analog or inhibitor of serine protease activity or a functional derivative thereof.

Embodiments of the present invention provide for methods for treating a subject in need of an immunotolerance therapy. In accordance with these embodiments, a subject may be treated with a composition for reducing the risk of a dysfunctional immune responses or a side-effect of a dysfunctional immune response in a subject. In another embodiment, methods herein provide for inducing immune tolerance specific for a graft and/or reduce the need for immunosuppressive therapy. In accordance with this embodiment, the immune system of the transplant recipient may have reduced or lost the specific ability to attack the graft while maintaining its ability to mount any other type of immune attack. In accordance with this method the subject can be administered a composition including a compound that is capable of significantly reducing serine protease activity or other activity associated with $\alpha$1-antitrypsin or $\alpha$1-antitrypsin analog. In certain embodiments, a composition capable of significantly reducing serine protease activity can include alpha-1-antitrypsin, an analog thereof or a combination thereof. In accordance with these embodiments, one example for immunotolerance therapy can include inhibiting cytokine production.

Embodiments of the present invention provide for methods for reducing TNF$\alpha$ (tumor necrosis factor alpha) levels in a subject including administering a composition including alpha-1-antitrypsin, an analog thereof or a combination thereof to a subject in need of such a treatment.

Embodiments of the present invention provide for methods for treating a subject in need of an immunotolerance therapy. In accordance with these embodiments methods are provided for reducing NO production and/or reducing apoptosis and/or inhibiting cytomegalovirus (infection and reactivation) including administering a composition including a compound that is capable of significantly reducing serine protease activity and/or other alpha-1-antitrypsin activity. In certain embodiments of the invention, a composition capable of significantly reducing serine protease activity and/or mimicking other alpha-1-antitrypsin activity can include alpha-1-antitrypsin, an analog thereof, or a combination thereof.

In certain embodiments of the present invention, the anti-inflammatory compound or immunomodulatory drug can include, but is not limited to, one or more of interferon, interferon derivatives including betaseron, beta-interferon, prostane derivatives including iloprost, cicaprost; glucocorticoids including cortisol, prednisolone, methyl-prednisolone, dexamethasone; immunosuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

Embodiments of the present invention provide for methods for reducing graft rejection in a subject. In accordance with these embodiments, a subject may be treated with a composition for reducing the risk of graft rejection responses or a side-effect of a graft rejection response in a subject. In accordance with this method, the subject can be administered a composition including a compound that is capable of significantly reducing serine protease activity. In certain embodiments, a composition capable of significantly reducing serine protease activity can include α1-antitrypsin, an analog thereof or a combination thereof. In one example, reducing graft rejection may include reducing the symptoms associated with graft rejection in a subject having an organ transplant, such as a kidney transplant or a bowel transplant or a non-organ transplant, such as a bone marrow transplant soft tissue transplant.

In yet another embodiment, the present invention may include combination therapies including compositions exhibiting α1-antitrypsin, an analog thereof, or substance with serine protease inhibitor activity. For example, a composition may include α1-antitrypsin and another serine protease inhibitor administered simultaneously or in separate compositions.

In accordance with embodiments disclosed herein, any of the disclosed compositions may be used to ameliorate symptoms associated with a transplant. These symptoms may include, but are not limited to, infiltration of graft with cells and/or serum factors (for example, complement, anti-graft antibodies), increased cytokine and/or chemokine production, increased nitric oxide production, increased apoptosis and cell death, and increased immune response against the transplant tissue and/or cells.

In another aspect, the present invention provides for a method of ameliorating a symptom or sign associated with transplantation in a subject in need of said amelioration. In accordance with this embodiment, a composition may be administered to a subject such as a pharmaceutically effective amount of a substance of α1-antitrypsin, an analog thereof or serine protease inhibitor activity, wherein the composition is capable of reducing, preventing or inhibiting serine protease or protease activity and/or binds to the sec receptor or other activity.

In certain embodiments, synthetic and/or naturally occurring peptides may be used in compositions and methods of the present invention for example, providing serine protease inhibitor activity. Homologues, natural peptides, with sequence homologies to AAT including peptides directly derived from cleavage of AAT may be used or other peptides such as, peptides that inhibit serine proteases or have AAT-like activity. Other peptidyl derivatives, e.g., aldehyde or ketone derivatives of such peptides are also contemplated herein. Without limiting to AAT and peptide derivatives of AAT, compounds like oxadiazole, thiadiazole and triazole peptoids and substances comprising certain phenylenedialkanoate esters, CE-2072, UT-77, and triazole peptoids may be used. Examples of analogues are TLCK (tosyl-L-lysine chloromethyl ketone) or TPCK (tosyl-L-phenylalanine chloromethyl ketone).

In other embodiments, an agent that reduces the occurrence of graft rejection, promotes prolonged graft function or promotes prolonged allograft survival can also be an inhibitor of serine protease activity, an inhibitor of elastase, or an inhibitor of proteinase-3. An inhibitor of serine protease activity can include, but is not limited to, small organic molecules including naturally-occurring, synthetic, and biosynthetic molecules, small inorganic molecules including naturally-occurring and synthetic molecules, natural products including those produced by plants and fungi, peptides, variants of α1-antitrypsin, chemically modified peptides, and proteins.

In some embodiments, AAT peptides contemplated for use in the compositions and methods of the present invention are also intended to include any and all of those specific AAT peptides other than the 10 amino acid AAT peptides of SEQ ID NO. 1 depicted supra. Any combination of consecutive amino acids depicting a portion of AAT or AAT-like activity may be used, such as amino acids 2-12, amino acids 3-13, 4-14, etc. of SEQ ID NO. 1, as well as any and all AAT peptide fragments corresponding to select amino acids of SEQ ID NO. 1. Applicants are herein entitled to compositions based upon any and all AAT peptide variants based upon the amino acid sequence depicted in SEQ ID NO. 1.

In one aspect of the invention, the pharmaceutical compositions of the present invention are administered orally, systemically, via an implant, intravenously, topically, intrathecally, intratracheally, intracranially, subcutaneously, intravaginally, intraventricularly, intranasally such as inhalation, mixed with grafts by flushing of organ or suspension of cells, or any combination thereof.

As such, those skilled in the art will appreciate that the conception, upon which this disclosure is based, can readily be used as a basis for designing other methods for carrying out the several features and advantages of the present invention.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

DESCRIPTION OF ILLUSTRATIVE EMBODIMENTS

Definitions

Figure 1A:
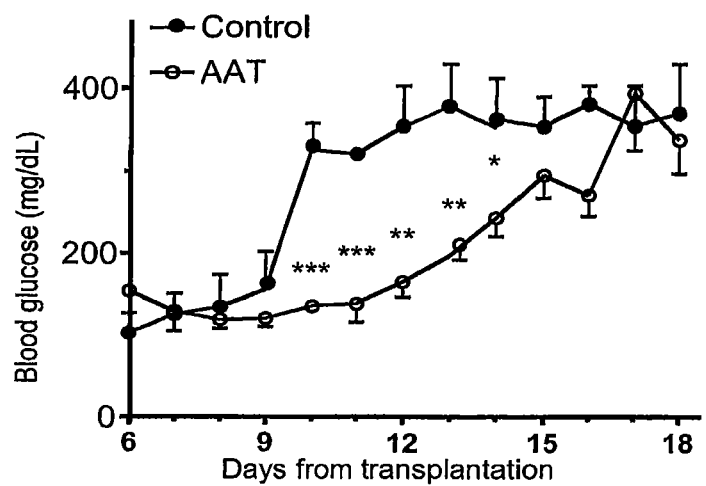
FIGS. 1A-1D illustrate an exemplary method of treating islet allografts with AAT. Islets from DBA/2 mice (H-2d) were transplanted under the renal capsule of streptozotocin-induced hyperglycemic C57BL/6 mice (H-2b). (A) Glucose levels from days 6-18. (B) Treatment protocols. Control and full AAT treatment are described in panel A. Early AAT treatment consists of treatment on days −1, 1 and 3 (2 mg, n=3). Late AAT treatment consists of treatment from day 2 and on every 2 days (2 mg, n=3). (C) Effect of mouse antihuman-AAT antibodies. Dashed line indicates post transplantation glucose levels of a mouse under full AAT treatment protocol (see A, B) that was immunized by multiple administrations of human AAT prior to transplantation (1 representative, n=3). Solid line indicates glucose levels of a non-immunized mouse treated under full AAT treatment protocol (1 representative, n=10). Arrow indicates detection of treatment-induced, antihuman-AAT antibodies in the non-immunized representative mouse. (D) Comparison of day 15 post-transplantation glucose levels in mice that were under full treatment protocol with ALB (n=3) or AAT (non-immunized n=10, immunized n=3). Of the AAT-treated group, antibodies were detected on day 15 in 3/3 immunized mice and in 6/10 non-immunized mice.

Terms that are not otherwise defined herein are used in accordance with their plain and ordinary meaning.

As used herein, "a" or "an" may mean one or more than one of an item.

As used herein, "analog of alpha-1-antitrypsin" may mean a compound having alpha-1-antitrypsin-like activity. In one embodiment, an analog of alpha-1-antitrypsin is a functional derivative of alpha-1-antitrypsin. In a particular embodiment, an analog of alpha-1-antitrypsin is a compound capable of significantly reducing serine protease activity. For example, an inhibitor of serine protease activity has the capability of inhibiting the proteolytic activity of trypsin, elastase, kallikrein, thrombin, cathepsin G, chymotrypsin, plasminogen activators, plasmin and/or other serine proteases.

As used herein, "immunomodulatory drugs or agents", it is meant, e.g., agents which act on the immune system, directly or indirectly, e.g., by stimulating or suppressing a cellular activity of a cell in the immune system, e.g., T-cells, B-cells, macrophages, or antigen presenting cells (APC, dendritic cells), or by acting upon components outside the immune system which, in turn, stimulate, suppress, or modulate the immune system, e.g. cytokines, e.g., hormones, receptor agonists or antagonists, and neurotransmitters; immunomodulators can be, e.g., immunosuppressants or immunostimulants.

It is to be understood that the terminology and phraseology employed herein are for the purpose of description and should not be regarded as limiting.

DETAILED DESCRIPTION OF THE INVENTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

Embodiments of the present invention provide for methods for treating a subject having or in need of a transplant. In accordance with these embodiments, a subject may be treated with a composition capable of significantly reducing serine protease activity. In addition, one embodiment of the present invention provides for methods including treating a subject with a composition comprising a compound having α-1-antitrypsin activity. In one embodiment, the composition can include α-1-antitrypsin, analog thereof or a serine protease inhibitor to for example, promote transplant survival or reduce a side effect of the transplant. Further, the administration of the composition can be before transplantation, during transplantation, after transplantation or combination thereof. In addition, the composition may further include one or more additional therapies such as immunosuppressive therapies. A transplant of the present invention may include transplantation of an organ such as lung, kidney, heart, liver, skin, pancreas, or bowel organ or non-organ such bone marrow, pancreatic islet, cornea, and/or soft tissue.

Serine protease inhibitors, have been found in a variety of organisms. At least nine separate, well-characterized proteins are now identified, which share the ability to inhibit the activity of various proteases. Several of the inhibitors have been grouped together, such as the $\alpha_1$-antitrypsin-proteinase inhibitor. Serine proteases include, but are not limited to, leukocyte elastase, thrombin, cathepsin G, chymotrypsin, plasminogen activators, and plasmin.

Embodiments of the present invention provide for methods for promoting transplantation, graft survival, reducing graft rejection and/or reducing or preventing side effects associated with graft rejection. In accordance with these embodiments, side-effects may include conditions associated with graft versus host disease (GVHD), or graft rejection. In one example, methods disclosed herein may be used to treat a subject undergoing bone marrow transplantation. In another embodiment, symptoms or signs may include, but are not limited to, one or more of the following, malaise, fever, dry cough, myalgias, and chest pains, ventilatory compromise, sweating, nausea, vomiting, fever, abdominal pain, bloody diarrhea, mucosal ulcerations, reduced renal function (increased creatinine, decreased urine output), reduced pulmonary function (increased shortness of breath, fever, cough, sputum, hypoxemia), reduced cardiac function (shortness of breath, chest pain, fatigue, pulmonary or peripheral edema, valvulopathy), reduced islet function (increased glucose, diabetes mellitus), graft versus host disease (gastrointestinal (GI) ulceration, pulmonary failure, skin ulceration).

Embodiments of the present invention provide for methods for treating a subject in need of an immunotolerance therapy. In accordance with these embodiments, a subject may be treated with a composition for inducing immune tolerance. This achieved while reducing the risk of a dysfunctional immune responses or a side-effect of a dysfunctional immune response in a subject as typically encountered during standard immune suppression. For example, a dysfunctional immune response may be an effect of graft rejection, pneumonia, sepsis, fungal infection, cancer. In accordance with this method, the subject can be administered a composition including a compound that is capable of significantly reducing serine protease activity or other activity associated with α1-antitrypsin or α1-antitrypsin analog. In certain embodiments, a composition capable of significantly reducing serine protease activity can include α-1-antitrypsin, an analog thereof or a combination thereof. In accordance with these embodiments, one example for immunotolerance therapy can include inhibiting cytokine production.

Any of the embodiments detailed herein may further include one or more a therapeutically effective amount of anti-microbial drugs anti-inflammatory agent, immunomodulatory agent, or immunosuppressive agent or combination thereof.

Non-limiting examples of anti-rejection agents/drugs may include for example cyclosporine, azathioprine, corticosteroids, FK506 (tacrolimus), RS61443, mycophenolate mofetil, rapamycin (sirolimus), mizoribine, 15-deoxyspergualin, and/or leflunomide or any combination thereof.

In addition, other combination compositions of methods disclosed in the present invention include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. Antibody-based therapies may be used as induction therapy and/or anti-rejection drugs in combination with the compositions and methods of the present invention.

Embodiments of the present invention provide for methods treating a subject in need of an immunotolerance therapy. In accordance with these embodiments, a subject may be treated with a composition capable of significantly reducing serine protease activity. In one embodiment, the composition can include α-1-antitrypsin, analog thereof or a serine protease inhibitor to for example, to reduce or inhibit the production of cytokines. In accordance with these embodiments, combination therapies are contemplated, such as combining α-1-antitrypsin composition with an anti-inflammatory agent.

In one particular embodiment, the present inventions provide for methods for reducing levels and activities of cytokines such as TNFα (tumor necrosis factor alpha). For example, the composition can include alpha-1-antitrypsin or analog thereof or combination thereof alone or in combination with other therapies.

In one embodiment, the reduction, prevention or inhibition of rejection of transplantation or side effects thereof associated with one or more of each of the above-recited conditions may be about 10-20%, 30-40%, 50-60%, or more reduction or inhibition due to administration of the disclosed compositions.

In one embodiment of the present invention a composition may include compounds that engage molecules for the SEC receptor to treat a subject undergoing a transplantation and/or in need of immunotolerance therapy. In each of the recited methods, an at-antitrypsin (e.g. mammalian derived) or inhibitor of serine protease activity substance contemplated for use within the methods of the present invention can include a series of peptides including carboxyterminal amino acid peptides corresponding to AAT. These pentapeptides can be represented by a general formula (I): I-A-B-C-D-E-F-G-H-II (note: in the Sequence Listing F=X), wherein I is Cys or absent; A is Ala, Gly, Val or absent; B is Ala, Gly, Val, Ser or absent; Cis Ser, Thr or absent; Dis Ser, Thr, Ans, Glu, Arg, Ile, Leu or absent; E is Ser, Thr, Asp or absent; F is Thr, Ser, Asn, Gln, Lys, Trp or absent; G is Tyr or absent; H is Thr, Gly, Met, Met(O), Cys, Thr or Gly; and II is Cys, an amide group, substituted amide group, an ester group or absent, wherein the peptides includes 4 or more consecutive amino acids and physiologically acceptable salts thereof. Among this series of peptides, several are equally acceptable including FVFLM (SEQ ID NO.1), FVFAM (SEQ. ID NO.2), FVALM (SEQ. ID NO.3), FVFLA (SEQ. ID NO.4), FLVFI (SEQ. ID NO.5), FLMII (SEQ. ID NO.6), FLFVL (SEQ. ID NO.7), FLFVV (SEQ. ID NO.8), FLFLI (SEQ. ID NO.9), FLFFI (SEQ. ID NO. 10), FLMFI (SEQ. ID NO. 11), FMLLI (SEQ. ID NO. 12), FIIMI (SEQ. ID NO. 13), FLFCI (SEQ. ID NO. 14), FLFAV SEQ. ID NO. 15), FVYLI (SEQ. ID NO. 16), FAFLM (SEQ. ID NO. 17), A VFLM (SEQ. ID NO. 18), and any combination thereof.

In several embodiments herein, AAT peptides contemplated for use in the compositions and methods of the present invention are also intended to include any and all of those specific AAT peptides of SEQ ID NO. 1 depicted supra. Any combination of consecutive amino acids simulating AAT or AAT-like activity may be used, such as amino acids 2-12, amino acids 3-14, 4-16, etc.

In each of the above-recited methods, at-antitrypsin or analogs thereof are contemplated for use in a composition herein. These analogs may include peptides. The peptides may include, but are not limited to, amino acid peptides containing MPSSVSWGIL (SEQ. ID NO. 19); LAGLCCLVPV (SEQ. ID NO. 20); SLAEDPQGDA (SEQ. ID NO. 21); AQKTDTSHHD (SEQ. ID NO. 22); QDHPTFNKIT (SEQ. ID NO. 23); PNLAEFAFSL (SEQ. ID NO. 24); YRQLAHQSNS (SEQ. ID NO. 25); TNIFFSPVSI (SEQ. ID NO. 26); ATAFAMLSLG (SEQ. ID NO. 27); TKADTHDEIL (SEQ. ID NO. 28); EGLNFNLTEI (SEQ. ID NO. 29); PEAQIHEGFQ SEQ. ID NO. 30); ELLRTLNQPD (SEQ. ID NO. 31); SQLQLTTGNG (SEQ. ID NO. 32); LFLSEGLKLV (SEQ. ID NO. 33); DKFLEDVKKL (SEQ. ID NO. 34); YHSEAFTVNF (SEQ. ID NO. 35); GDHEEAKKQI (SEQ. ID NO. 36); NDYVEKGTQG (SEQ. ID NO. 37); KIVDLVKELD (SEQ. ID NO. 38); RDTVFALVNY (SEQ. ID NO. 39); IFFKGKWERP (SEQ. ID NO. 40); FEVKDTEDED (SEQ. ID NO. 41); FHVDQVTTVK (SEQ. ID NO. 42); VPMMKRLGMF (SEQ. ID NO. 43); NIQHCKKLSS (SEQ. ID NO. 44); WVLLMKYLGN (SEQ. ID NO. 45); ATAIFFLPDE (SEQ. ID NO. 46); GKLQHLENEL (SEQ. ID NO. 47); THDIITKFLE (SEQ. ID NO. 48); NEDRRSASLH (SEQ. ID NO. 49); LPKLSITGTY (SEQ. ID NO. 50); DLKSVLGQLG (SEQ. ID NO. 51); ITKVFSNGAD (SEQ. ID NO. 52); LSGVTEEAPL (SEQ. ID NO. 53); KLSKA VHKA V (SEQ. ID NO. 54); LTIDEKGTEA (SEQ. ID NO. 55); AGAMFLEAIP (SEQ. ID NO. 56); MSIPPEVKFN (SEQ. ID NO. 57); KPFVFLMIEQ (SEQ. ID NO. 58); NTKSPLFMGK (SEQ. ID NO. 59); VVNPTQK (SEQ. ID NO. 60), or any combination thereof.

In accordance with embodiments of the present invention, the peptide can be protected or derivatized in by any means known in the art for example, N-terminal acylation, C-terminal amidation, cyclization, etc. In a specific embodiment, the N-terminus of the peptide is acetylated.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (i.e. pharmaceutical chemical, protein, gene, antibody etc. of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regimen may be adjusted to provide the optimum therapeutic response.

In one embodiment, the compound (i.e. pharmaceutical chemical, protein, peptide etc. of the embodiments) may be administered in a convenient manner such as subcutaneous, intravenous, by oral administration, inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the compound may be administered intranasally, such as inhalation.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition cannot be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound (e.g. a compound that reduces serine protease activity) in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art.

Solutions of the active compounds as free-base or pharmacologically acceptable salts can be prepared in water suitably mixed with a surfactant, such as hydroxypropyl cellulose. Dispersions can also be prepared in glycerol, liquid polyethylene glycols, and mixtures thereof and in oils. Under ordinary conditions of storage and use, these preparations contain a preservative to prevent the growth of microorganisms. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

A pharmaceutical composition may be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

Pharmaceutical compositions are administered in an amount, and with a frequency, that is effective to inhibit or alleviate side effects of a transplant and/or to reduce or prevent rejection. The precise dosage and duration of treatment may be determined empirically using known testing protocols or by testing the compositions in model systems known in the art and extrapolating therefrom. Dosages may also vary with the severity of the condition. A pharmaceutical composition is generally formulated and administered to exert a therapeutically useful effect while minimizing undesirable side effects. In general, an oral dose ranges from about 200 mg to about 1000 mg, which may be administered for example 1 to 3 times per day.

It will be apparent that, for any particular subject, specific dosage regimens may be adjusted over time according to the individual need. The preferred doses for administration can be anywhere in a range between about 0.01 mg and about 100 mg per ml of biologic fluid of treated patient. In one particular embodiment, the range can be between 1 and 100 mg/kg which can be administered daily, every other day, biweekly, weekly, monthly etc. In another particular embodiment, the range can be between 10 and 75 mg/kg introduced weekly to a subject. The therapeutically effective amount of $\alpha$1-antitrypsin, peptides, or drugs that have similar activities as $\alpha$1-antitrypsin or peptides can be also measured in molar concentrations and can range between about 1 nM to about 2 mM.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent.

Liposomes can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

In a preferred embodiment, a nucleic acid (e.g. $\alpha$1-antitrypsin or analogs thereof) and the lipid dioleoylphosphatidylcholine may be employed. For example, nuclease-resistant oligonucleotides may be mixed with lipids in the presence of excess t-butanol to generate liposomal-oligonucleotides for administration.

The pharmaceutical compositions containing the $\alpha$1-antitrypsin, analog thereof, or inhibitor of serine protease activity or a functional derivative thereof may be administered to individuals, particularly humans, for example by subcutaneously, intramuscularly, intranasally, orally, topically, transdermally, parenterally, gastrointestinally, transbronchially and transalveolarly. Topical administration is accomplished via a topically applied cream, gel, rinse, etc. containing therapeutically effective amounts of inhibitors of serine proteases. Transdermal administration is accomplished by application of a cream, rinse, gel, etc. capable of allowing the inhibitors of serine proteases to penetrate the skin and enter the blood stream. In addition, osmotic pumps may be used for administration. The necessary dosage will vary with the particular condition being treated, method of administration and rate of clearance of the molecule from the body.

In each of the aforementioned compositions and methods, a compound having serine protease inhibitor activity and/or having $\alpha$1-antitrypsin activity or analog thereof may be used in a single therapeutic dose, acute manner or a chronic manner to treat episodes or prolonged bouts, respectively, in promoting graft survival, treating graft rejection and/or associated graft rejection-induced side-effects.

In certain embodiments of the methods of the present invention, the subject may be a mammal such as a human or a veterinary and/or a domesticated animal.

Therapeutic Methods

In one embodiment of the present invention, methods provide for treating a subject in need of or undergoing a transplant. For example, treatments for reducing graft rejection, promoting graft survival, and promoting prolonged graft function by administering to a subject in need thereof a therapeutically effective amount of a composition. The composition can include a compound capable of inhibiting at least one serine protease for example, $\alpha$1-antitrypsin, or analog thereof.

Preserving the Graft During Transplant Before Engraftment

According to the methods of the present invention, transplantation complications can be reduced or inhibited to obtain important therapeutic benefits. Therefore, administration of a therapeutic composition contemplated by embodiments of the invention, i.e., α1-antitrypsin, derivative or analog thereof, can be beneficial for the treatment of transplantation complications or conditions.

Another beneficial effect of use of the compositions and methods of the present invention include reducing negative effects on an organ or non-organ during explant, isolation, transport and/or prior to implantation. For example, the composition can reduce apoptosis, reduce production of cytokines, reduce production of NO, or combination thereof in an organ for transplant. In one particular embodiment, a composition can include a compound that includes alpha-1-antitrypsin, an analog thereof, a serine protease inhibitor, serine protease inhibitor-like activity, analog thereof or a combination thereof. The transplant organ or non-organ can include, but is not limited to, lung, kidney, heart, liver, soft tissue, skin, pancreas, intestine, soft tissue cornea, bone marrow, stern cell, pancreatic islet, and combination thereof.

In a further embodiment, the methods and compositions of the invention are useful in the therapeutic treatment of graft rejection associated side effects. In a yet further embodiment, graft rejection associated side effects can be prevented by the timely administration of the agent of the invention as a prophylactic, prior to onset of one or more symptoms, or one or more signs, or prior to onset of one or more severe symptoms or one or more signs of a graft rejection associated disease. Thus, a patient at risk for a particular graft rejection or graft rejection-associated disease or clinical indication can be treated with serine protease inhibitors, for example, (Benzyloxycarbonyl)-L-Valyl-N-[1-(3-(5-(3-Trifluorornethylbenzyl)-1,2,4-oxadiazolyl)carbonyl)-2-(S)-Methylpropyl]-L-Prolinarnide; as a prophylactic measure.

It is contemplated herein that the present compositions and methods of the present invention can be used to treat patients with one or more grafts who require chronic therapy to maintain graft integrity, and such patients will therefore benefit from indefinite or chronic use of the rejection repressive therapy of the methods of the present invention. Yet another embodiment can be used to treat flairs of acute rejection so as to minimize the effects of acute clinical rejection, organ failure, and/or eventual destruction of the graft.

Desirable blood levels may be maintained by continuous infusion to provide about 0.01-5.0 mg/kg/hr or by intermittent infusions containing about 0.4-20 mg/kg of the active ingredient(s). Buffers, preservatives, antioxidants and the like can be incorporated as required. It is intended herein that the ranges recited also include all those specific percentage amounts between the recited range. For example, the range of about 0.4 to 20 mg/kg also encompasses 0.5 to 19.9%, 0.6 to 19.8%, etc., without actually reciting each specific range therewith.

Serine Protease Inhibitors

It is to be understood that the present invention is not limited to the examples described herein, and other serine proteases known in the art can be used within the limitations of the invention. For example, one skilled in the art can easily adopt inhibitors as described in WO 98/24806, which discloses substituted oxadiazole, thiadiazole and triazole as serine protease inhibitors. U.S. Pat. No. 5,874,585 discloses substituted heterocyclic compounds useful as inhibitors of serine proteases for example, (benzyloxycarbonyl)-Lvalyl-N-[1-(3-(5-(3-trifluoromethylbenzyl)-1,2,4-oxa diazolyl) carbonyl)-2-(S)methylpropyl]-L-prolinamide benzyloxycarbonyl)-L-valyl-N-[1-(3-(5-(2-phenylethyl)-1,2,4-oxadiazolyl)carbonyl)-2-(S)-methylpropyl]-L-prolinamide; and (benzyloxycarbonyl)-L-valylN-[1-(3-(5-(2-methoxybenzyl)-1,2,4-oxadiazolyl)carbonyl)-2-(S)-methylpropyl]-Lprolinamide.

α1-antitrypsin is a glycoprotein of MW 51,000 with 417 amino acids and 3 oligosaccharide side chains. Human α1-antitrypsin is a single polypeptide chain with no internal disulfide bonds and only a single cysteine residue normally intermolecularly disulfide-linked to either cysteine or glutathione. The reactive site of α1-antitrypsin contains a methionine residue, which is labile to oxidation upon exposure to tobacco smoke or other oxidizing pollutants. Such oxidation reduces the elastase-inhibiting activity of α1-antitrypsin; therefore substitution of another amino acid at that position, i.e. alanine, valine, glycine, phenylalanine, arginine or lysine, produces a form of at-antitrypsin which is more stable. α1-antitrypsin can be represented by the following formula: SEQ. ID NO. 61:

```
MPSSVSWGIL LAGLCCLVPV SLAEDPQGDA AQKTDTSHHD

QDHPTFNKITPNLAEFAFSL YRQLAHQSNS TNIFFSPVSI ATAFAMLSLG

TKADTHDEIL                                                    100

EGLNFNLTEI PEAQIHEGFQ ELLRTLNQPD SQLQLTTGNG

LFLSEGLKLVDKFLEDVKKL YHSEAFTVNF GDHEEAKKQI NDYVEKGTQG

KIVDLVKELD                                                    200

RDTVFALVNY IFFKGKWERP FEVKDTEDED FHVDQVTTVK VPMMKRLGMF

NIQHCKKLSS WVLLMKYLGN ATAIFFLPDE GKLQHLENEL THDIITKFLE 300

NEDRRSASLH LPKLSITGTY DLKSVLGQLG ITKVFSNGAD LSGVTEEAPL

KLSKAVHKAV LTIDEKGTEA AGAMFLEAIP MSIPPEVKFN KPFVFLMIEQ 400

NTKSPLFMGK VVNPTQK                                            417
```

One important amino acid sequence near the carboxyterminal end of α1-antitrypsin is shown in bold and underlined and is pertinent to this invention (details of the sequence can be found for example in U.S. Pat. No. 5,470,970, as incorporated by reference).

Extrahepatic sites of AAT production include neutrophils, monocytes and macrophages, and the expression of AAT is inducible in response to LPS, TNFα, IL-1 and IL-6 in various cell types. Deficiency in AAT is associated with immune dysfunctional conditions such as rheumatoid arthritis and systemic lupus erythematosus.

Other serine protease inhibitor molecules, which may be used in any of the disclosed compositions may include compounds disclosed in the following: WO 98/20034 disclosing serine protease inhibitors from fleas; W098/23565 disclosing aminoguanidine and alkoxyguanidine compounds useful for inhibiting serine proteases; W098/50342 disclosing bis-aminomethylcarbonyl compounds useful for treating cysteine and serine protease disorders; W098/50420 cyclic and other amino acid derivatives useful for thrombin-related diseases; WO 97/21690 disclosing D-amino acid containing derivatives; WO 97110231 disclosing ketomethylene group-containing inhibitors of serine and cysteine proteases; WO 97/03679 disclosing phosphorous containing inhibitors of serine and cysteine proteases; WO98/21186 benzothiazo and related heterocyclic inhibitors of serine proteases; WO 98/22619 disclosing a combination of inhibitors binding to P site of serine proteases with chelating site of divalent cations; WO 98/22098 disclosing a composition which inhibits conversion of proenzyme CPP32 subfamily including caspase 3 (CPP32/Yama/Apopain); WO 97/48706 disclosing pyrrolo-pyrazine-diones; and WO 97/33996 disclosing human placental bikunin (recombinant) as serine protease inhibitor.

Other compounds having serine protease inhibitory activity are equally suitable and effective for use in the methods of the present invention, including but not limited to: tetrazole derivatives as disclosed in WO 97/24339; guanidinobenzoic acid derivatives as disclosed in WO 97/37969 and in a number of U.S. Pat. Nos. 4,283,418; 4,843,094; 4,310,533; 4,283,418; 4,224,342; 4,021,472; 5,376,655; 5,247,084; and 5,077,428; phenylsulfonylamide derivatives represented by general formula in WO 97/45402; novel sulfide, sulfoxide and sulfone derivatives represented by general formula in WO 97/49679; novel amidino derivatives represented by general formula in WO 99/41231; other amidinophenol derivatives as disclosed in U.S. Pat. Nos. 5,432,178; 5,622,984; 5,614,555; 5,514,713; 5,110,602; 5,004,612; and 4,889,723 among many others.

Graft Rejection and Graft Survival-Side-Effects and Conditions

One of the beneficial effects of use of the compositions and methods of the present invention include, for example, and not by way of limitation, reduced infiltration of graft with cells or serum factors (including but not limited to, complement, anti graft antibody that generate inflammation and graft rejection), reduced cytokines, reduced nitric oxide, reduced apoptosis, and reduced specific immune response against the graft or any combination thereof.

Management of Graft Rejection

By preventing or reducing the side effects or conditions associated with graft survival or graft rejection using this novel approach, several advantages are obtained compared to alternative approaches, for example, and not by way of limitation:

1. Reduced infiltration of graft with cells or serum factors (for example, and not by way of limitation, complement, anti graft antibody that generate inflammation and graft rejection); reduced production of cytokines or nitric oxide (NO) that can induce inflammation or apoptosis; inhibits apoptosis; inhibits immune activation, inhibits CMV or any combination thereof.

2. Synthetic inhibitors of serine proteases (AAT-like mimics or analogs) can and have been developed by means known in the art. Such a pharmaceutical agent may be formulated as for example, a cream to treat graft rejection and/or promote graft survival.

3. Commercially available agents already approved for different use in humans will work as a treatment for graft rejection and/or promote graft survival. These agents are currently used for indications other than graft rejection and/or to promote graft survival, and include injectible AAT, plasma preparations, aprotinin and others (American J. of Resp Critical Care Med 1998, VII 158: 49-59, incorporated herein by reference in its entirety). In one embodiment, serine protease inhibitors may be delivered by inhalation. An inhaled agent (natural AAT or a synthetic AAT-like mimic/or other inhibitor of serine protease) may be especially useful due to elevated local concentrations, ease of drug delivery, and lack of side effects (since administration is not systemic). This mode of focused drug delivery may augment serine protease inhibitor activity within the lung tissues and associated lymphatics, which are two of the principal sites where diseases and/or clinical conditions associated with graft rejection and/or promotion of graft survival develop.

4. By promoting graft survival and/or treating graft rejection, the direct cause of the side effect is disrupted in affected individuals. This invention specifically contemplates inhibiting host cell serine proteases or induce the SEC receptor or combination thereof as a method of treating graft rejection and/or promoting graft survival in a mammal in need thereof in conjunction with administration of one or more anti-rejection and/or anti-microbial.

5. There is an extensive clinical experience using indictable AAT to treat patients with genetic AAT deficiency. No long-term negative effects have been detected to date (American J. of Resp Critical Care Med 1998, VII 158: 49-59; Wencker et al. Chest 2001, 119:737-744). Moreover, a small molecule inhibitor of host serine protease has been administered to patients with Kawasaki's Disease (Ulinistatin, Ono pharmaceuticals).

Isolated Proteins for Use in the Compositions and Methods of the Invention

One aspect of the invention pertains to proteins, and portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

Recombinant unmodified and mutant variants of .alpha..sub.1-antitrypsin produced by genetic engineering methods are also known (see U.S. Pat. No. 4,711,848). The nucleotide sequence of human alpha.sub.1-antitrypsin and other human alpha.sub.1-antitrypsin variants has been disclosed in international published application No. WO 86/00,337, the entire contents of which are incorporated herein by reference. This nucleotide sequence may be used as starting material to generate all of the AAT amino acid variants and amino acid fragments depicted herein, using recombinant DNA techniques and methods known to those of skill in the art.

An isolated and/or purified or partially purified protein or biologically active portion thereof may be used in any embodiment of the invention. A protein that is substantially free of cellular material includes preparations of protein having less than about 30%, 20%, 10%, or 5% (by dry weight) of heterologous protein. When the protein or biologically active portion thereof is recombinantly produced, it can also be substantially free of culture medium. When the protein is produced by chemical synthesis, it is preferably substantially free of chemical precursors or other chemicals. Accordingly, such preparations of the protein have less than about 30%, 20%, 10%, and 5% (by dry weight) of chemical precursors or compounds other than the polypeptide of interest.

Biologically active portions of a polypeptide of the invention include polypeptides including amino acid sequences sufficiently identical to or derived from the amino acid sequence of the protein (e.g., the amino acid sequence shown in any of SEQ ID Nos: 1 to 60, which exhibit at least one activity of the corresponding full-length protein). A biologically active portion of a protein of the invention can be a polypeptide, which is, for example, 5, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID Nos: 1 to 60. Other useful proteins are substantially identical (e.g., at least about 45%, preferably 55%, 65%, 75%, 85%, 95%, or 99%) to any of SEQ ID NOs: 1 to 60, and retain the functional activity of the protein of the corresponding naturally-occurring protein yet differ in amino acid sequence due to natural allelic variation or mutagenesis.

The compounds of the present invention can be used as therapeutic agents in the treatment of a physiological (especially pathological) condition caused in whole or part, by excessive serine protease activity. In addition, a physiological (especially pathological) condition can be inhibited in whole or part. Peptides contemplated herein may be administered as free peptides or pharmaceutically acceptable salts thereof. The peptides should be administered to individuals as a pharmaceutical composition, which, in most cases, will include the peptide and/or pharmaceutical salts thereof with a pharmaceutically acceptable carrier.

When utilizing BLAST, Gapped BLAST, and PSI-Blast programs, the default parameters of the respective programs (e.g., XBLAST and NBLAST) can be used. See http://www.ncbi.nlm.nih.gov.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity.

Fusion Polypeptides

In other embodiments, compounds having serine protease inhibitor activity such as α1-antitrypsin and/or analog thereof, may be part of a fusion polypeptide. In one example, a fusion polypeptide may include α1-antitrypsin (e.g. mammalian α1-antitrypsin) or an analog thereof and a different amino acid sequence that may be heterologous to the α1-antitrypsin or analog substance.

In yet other embodiments, the fusion polypeptide contemplated for use in the methods of the present invention can additionally include an amino acid sequence that is useful for identifying, tracking or purifying the fusion polypeptide, e.g., a FLAG or HIS tag sequence. The fusion polypeptide can include a proteolytic cleavage site that can remove the heterologous amino acid sequence from the compound capable of serine protease inhibition, such as mammalian α1-antitrypsin or analog thereof.

In one embodiment, fusion polypeptides of the invention are produced by recombinant DNA techniques. Alternative to recombinant expression, a fusion polypeptide of the invention can be synthesized chemically using standard peptide synthesis techniques. The present invention also provides compositions that comprise a fusion polypeptide of the invention and a pharmaceutically acceptable carrier, excipient or diluent.

In particular, in one embodiment the fusion protein comprises a heterologous sequence that is a sequence derived from a member of the immunoglobulin protein family, for example, comprise an immunoglobulin constant region, e.g., a human immunoglobulin constant region such as a human IgG 1 constant region. The fusion protein can, for example, include a portion of α1-antitrypsin, analog thereof or inhibitor of serine protease activity polypeptide fused with the amino-terminus or the carboxyl-terminus of an immunoglobulin constant region, as disclosed, e.g., in U.S. Pat. No. 5,714,147, and U.S. Pat. No. 5,116,964. In accordance with these embodiments, the FcR region of the immunoglobulin maybe either wild-type or mutated. In certain embodiments, it is desirable to utilize an immunoglobulin fusion protein that does not interact with an Fc receptor and does not initiate ADCC reactions. In such instances, the immunoglobulin heterologous sequence of the fusion protein can be mutated to inhibit such reactions. See, e.g., U.S. Pat. No. 5,985,279 and WO 98/06248.

In yet another embodiment, α1-antitrypsin, analog thereof, or inhibitor of serine protease activity polypeptide fusion protein comprises a GST fusion protein in which is fused to the C-terminus of GST sequences. Fusion expression vectors and purification and detection means are known in the art.

Expression vectors can routinely be designed for expression of a fusion polypeptide of the invention in prokaryotic (e.g., E. coli) or eukaryotic cells (e.g., insect cells (using baculovirus expression vectors), yeast cells or mammalian cells) by means known in the art.

Expression of proteins in prokaryotes may be carried out by means known in the art. Such fusion vectors typically serve three purposes: 1) to increase expression of recombinant protein; 2) to increase the solubility of the recombinant protein; and 3) to aid in the purification of the recombinant protein by acting as a ligand in affinity purification.

In yet another embodiment, a nucleic acid of the invention is expressed in mammalian cells using a mammalian expression vector as described in the art. In another embodiment, the recombinant mammalian expression vector is capable of directing expression of the nucleic acid preferentially in a particular cell type (e.g., tissue-specific regulatory elements are used to express the nucleic acid) such as pancreas-specific promoters (Edlund et al. (1985) Science 230:912-916), and mammary gland-specific promoters (e.g., milk whey promoter; U.S. Pat. No. 4,873,316 and European Application Publication No. 264, 166). A host cell can be any prokaryotic (e.g., E. coli) or eukaryotic cell (e.g., insect cells, yeast or mammalian cells). Vector DNA can be introduced into prokaryotic or eukaryotic cells via conventional transformation or transfection techniques.

Combination Therapies

In each of the aforementioned methods of the present invention, the use of a compound capable of inhibiting serine protease or α1-antitrypsin or analog thereof alone or in combination with standard immunosuppressive agents enables transplantation of grafts into immunosuppressed or immunocompromised recipients. This combination therapy will expand the eligible patient population able to receive this form of treatment.

In each of the aforementioned aspects and embodiments of the invention, combination therapies other than those already enumerated above are also specifically contemplated herein. In particular, the compositions of the present invention may be administered with one or more macrolide or non-macrolide antibiotics, anti-bacterial agents, anti-fungals, anti-viral agents, and anti-parasitic agents. Examples of macrolide antibiotics that may be used in combination with the composition of the present invention include, but are not limited to, synthetic, semi-synthetic or naturally occurring macrolidic antibiotic compounds: methymycin, neomethymycin, YC-17, litorin, TMP-SSX, erythromycin A to F, and oleandomycin. Examples of preferred erythromycin and erythromycin-like compounds include: erythromycin, clarithromycin, azithromycin, and troleandomycin.

Examples of anti-bacterial agents include, but are not limited to, penicillins, quinolones, aminoglycosides, vancomycin, monobactams, cephalosporins, carbacephems, cephamycins, carbapenems, and monobactams and their various salts, acids, bases, and other derivatives.

Anti-fungal agents include, but are not limited to, caspofungin, terbinafine hydrochloride, nystatin, and selenium sulfide.

Anti-viral agents include, but are not limited to, ganciclovir, acyclovir, valacyclovir, amantadine hydrochloride, rimantadin and edoxudine.

Examples of macrolide antibiotics that may be used in combination with the composition of the present invention include, but are not limited to, synthetic, semi-synthetic or naturally occurring macrolidic antibiotic compounds: methymycin, neomethymycin, YC-17, litorin, TMP-SSX, erythromycin A to F, and oleandomycin. Examples of preferred erythromycin and erythromycin-like compounds include: erythromycin, clarithromycin, azithromycin, and troleandomycin.

Anti-parasitic agents include, but are not limited to, pirethrins/piperonyl butoxide, permethrin, iodoquinol, metronidazole, co-trimoxazole (sulfamethoxazole/trimethoprim), and pentamidine isethionate.

In another aspect, in the method of the present invention, one may, for example, supplement the composition by administration of a therapeutically effective amount of one or more an anti-inflammatory or immunomodulatory drugs or agents. By "anti-inflammatory drugs", it is meant, e.g., agents which treat inflammatory responses, i.e., a tissue reaction to injury, e.g., agents which treat the immune, vascular, or lymphatic systems.

Anti-inflammatory or immunomodulatory drugs or agents suitable for use in this invention include, but are not limited to, interferon derivatives, (e.g., betaseron); prostane derivatives, (e.g., compounds disclosed in PCT/DE93/0013, iloprost, cortisol, dexamethasone; immunosuppressives, (e.g., cyclosporine A, FK-506 (mycophenylate mofetil); lipoxygenase inhibitors, (e.g., zileutone, MK-886, WY-50295); leukotriene antagonists, (e.g., compounds disclosed in DE 40091171 German patent application P 42 42 390.2); and analogs; peptide derivatives, (e.g., ACTH and analogs); soluble TNF-receptors; TNF-antibodies; soluble receptors of interleukins, other cytokines, T-cell-proteins; antibodies against receptors of interleukins, other cytokines, and T-cell-proteins.

Kits

In still further embodiments, the present invention concerns kits for use with the methods described above. Small molecules, proteins or peptides may be employed for use in any of the disclosed methods. In addition, other agents such as anti-bacterial agents, immunosuppressive agents, anti-inflammatory agents may be provided in the kit. The kits thus can include, in suitable container means, a protein or a peptide or analog agent, and optionally one or more additional agents.

The kits may further include a suitably aliquoted composition of the encoded protein or polypeptide antigen, whether labeled or unlabeled, as may be used to prepare a standard curve for a detection assay.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Alpha-1-Antitrypsin Prolongs Graft Islet Graft Survival in Mice

FIGS. 1A-1D. Islets from DBA/2 mice (H-2d) were transplanted under the renal capsule of streptozotocin-induced hyperglycemic C57BL/6 mice (H-2b). (A) Glucose levels from days 6-18. Control consists of mice that were untreated (n=3) or treated from day −1 every 3 days with human albumin (ALB, 6 mg, n=3). Prolonged islet graft survival is observed in mice treated from day −1 every 3 days with human AAT (2 mg, n=10). * P<0.05,  P<0.01, * P<0.001 between glucose levels on same day. (B) Treatment protocols. Control and full AAT treatment are described in panel A. Early AAT treatment consists of treatment on days −1, 1 and 3 (2 mg, n=3). Late AAT treatment consists of treatment from day 2 and on every 2 days (2 mg, n=3). Rejection indicates the day that glucose levels exceed 300 mg/dl. (C) Effect of mouse anti-human-AAT antibodies. Dashed line indicates post transplantation glucose levels of a mouse under full AAT treatment protocol (see A, B) that was immunized by multiple administrations of human AAT prior to transplantation (1 representative, n=3). Solid line indicates glucose levels of a non-immunized mouse treated under full AAT treatment protocol (1 representative, n=10). Arrow indicates detection of treatment-induced, anti-human-AAT antibodies in the non-immunized representative mouse. (D) Comparison of day 15 post-transplantation glucose levels in mice that were under full treatment protocol with ALB (n=3) or AAT (non-immunized n=10, immunized n=3). Of the AAT-treated group, antibodies were detected on day 15 in 3/3 immunized mice and in 6/10 non-immunized mice.** P=0.005 between mice that produced antibodies (n=6) and mice that did not produce antibodies (n=4).

Figure 1B:
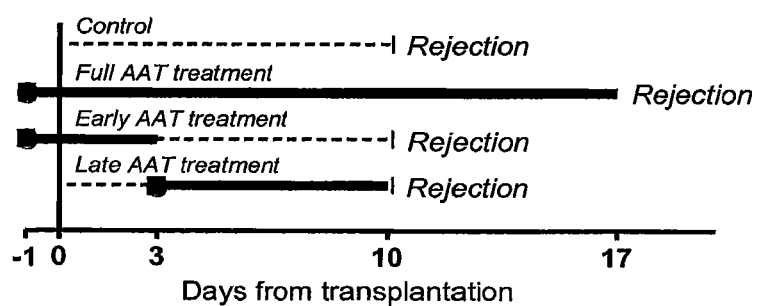

Treatment with human albumin (6 mg) resulted in graft rejection comparable to that of untreated recipient mice. In contrast, recipient mice that received AAT (2 mg) exhibited prolonged graft function. As depicted in FIG. 1b, neither of the partial treatment protocols, i.e., days −1, 1 and 3 ('early treatment') or days 2 and beyond ('late treatment') prolonged allograft survival.

Figure 1C:
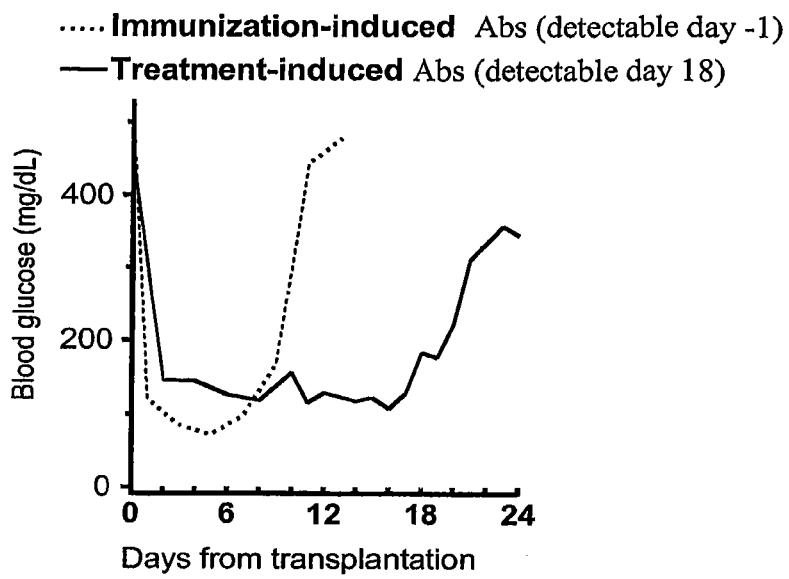
Figure 1D:
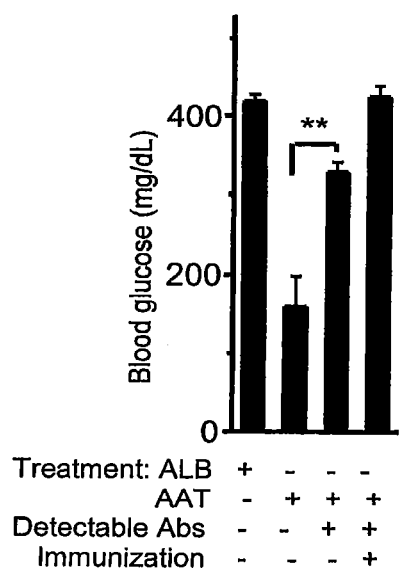

AAT-treated mice developed anti-human-AAT antibodies (FIGS. 1C and 1D). Individual mice exhibited anti-human-AAT antibodies at various time points (data not shown). To ascertain that the antibodies reduce the protective effect of AAT, a group of mice was pre-exposed ("immunized") to human AAT two months before being rendered hyperglycemic and transplanted with allogeneic islets. These graft recipients were treated with the full AAT protocol, despite exhibiting high titers of specific antibodies before engraftment, and displayed rapid graft rejection (FIG. 1C). Day 15 was chosen to depict an association between antibody formation and loss of AAT protective activity; at this time point AAT-treated mice were divided into positive and negative producers of anti-human AAT antibodies. As shown in FIG. 1D, on day 15 all antibody-positive mice were hyperglycemic and all antibody-negative mice were normoglycemic.

Example 2

Figure 2A:
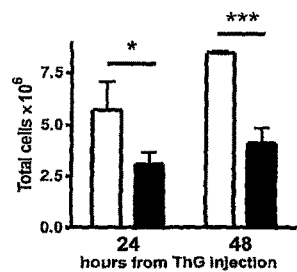
FIGS. 2A-2D illustrate an exemplary method of the effect of AAT on thioglycolate-elicited peritoneal cellular infiltrates. (A) Total cell population of lavaged cells of (o) saline or (Δ) AAT-treated (5 mg) thioglycolate-injected mice. (B) Percent cell population from saline-treated mice at 48 hours. (C) Oxidation of AAT. (D) Identification of elicited macrophages and neutrophils.
Figure 2B:
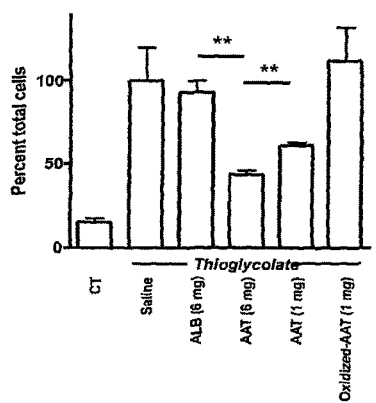
Figure 2C:
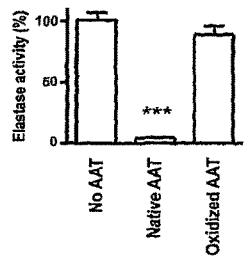
Figure 2D:
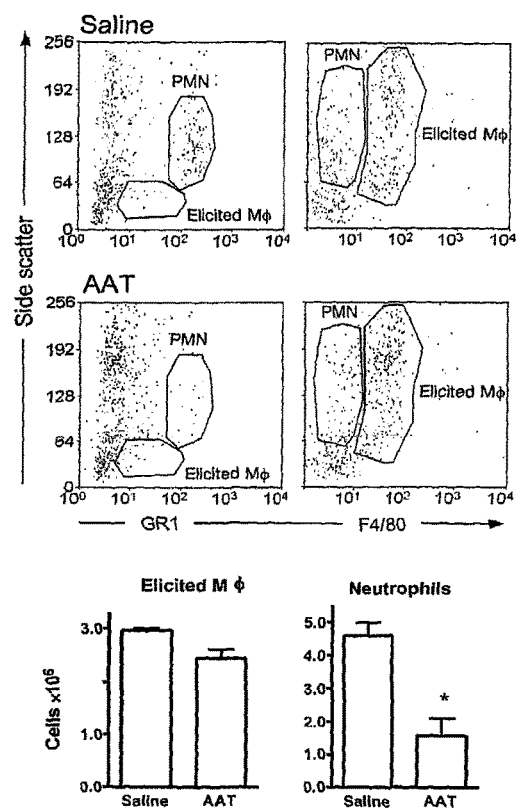

FIGS. 2A-2D illustrate an exemplary method of the effect of AAT on thioglycolate elicited peritoneal cellular infiltrates. Mice were administered intraperitoneal 0.1 ml saline, ALB, AAT or oxidized-AAT followed by 1 ml of saline or thioglycolate (ThG, 3% w/v, n=3 per group). Peritoneal lavage was performed on separate groups after 24 and 48 hours. (A) Total cell population of lavaged cells of (open bars) saline or (closed bars) AAT-treated (5 mg) thioglycolate-injected mice.  P<0.05. (B) Percent cell population from saline-treated mice at 48 hours.  P<0.05. (C) Oxidation of AAT. AAT was subjected to oxidative radicals (see Methods). Loss of serine protease activity of oxidized AAT was assessed in an elastase assay. Activity of elastase in the absence of native AAT was set at 100% and the percentage of activity in the presence of native and oxidized AAT was calculated (n=3). * * * P<0.001. In FIG. 2D, elicited macrophages and neutrophils are identified. Peritoneal infiltrates from 48 hour lavages of ALB (6 mg) and AAT-treated (6 mg), thioglycolate-injected mice were stained for FACS analysis by specific antibodies. Macrophages and neutrophils were identified on the basis of F4/80 and GR1 versus side scatter flow cytometry profiles. Top, FACS analysis representative graphs (n=3). Quantified FACS results (n=3) are depicted in the bottom.

AAT Inhibits Cellular Infiltration

To address the possibility that AAT affects effector cell infiltration, two models of cell emigration were examined: thioglycolate (ThG)-elicited peritoneal infiltration, and cellular infiltration due to intraperitoneal injection of MHC-incompatible fibroblasts.

As shown in FIG. 2A, there was a progressive increase in total cell count at 24 and 48 hours in mice injected with ThG, whereas no significant increase was observed in mice injected with AAT and ThG. At 48 hours, total cell count in peritoneal lavage of AAT-treated mice was 50% of that of control (FIG. 2B). Total cell count in mice that received albumin control was similar to that of saline-treated mice. There was a dose-dependent effect of AAT in that one-sixth the dose was found to reduce cell count to a lesser extent in a significant manner. Oxidized AAT, which had lost its in vitro anti-elastase activity (FIG. 2C), did not affect cellular infiltrate at 1 mg (FIG. 2B).

The decrease in total cell count is primarily attributed to a decrease in the number of neutrophils (FIG. 2D), identified by their GR-1 high/intermediate side-scatter (SSC) profile. No major difference was observed with the infiltration of macrophages, identified by their F4/80int, GR-int, intermediate SSC profile[12], which is distinct from the F4/80 very high, GR1low, high SSC profile of resident macrophages[12] (data not shown).

Example 3

Figure 3A:
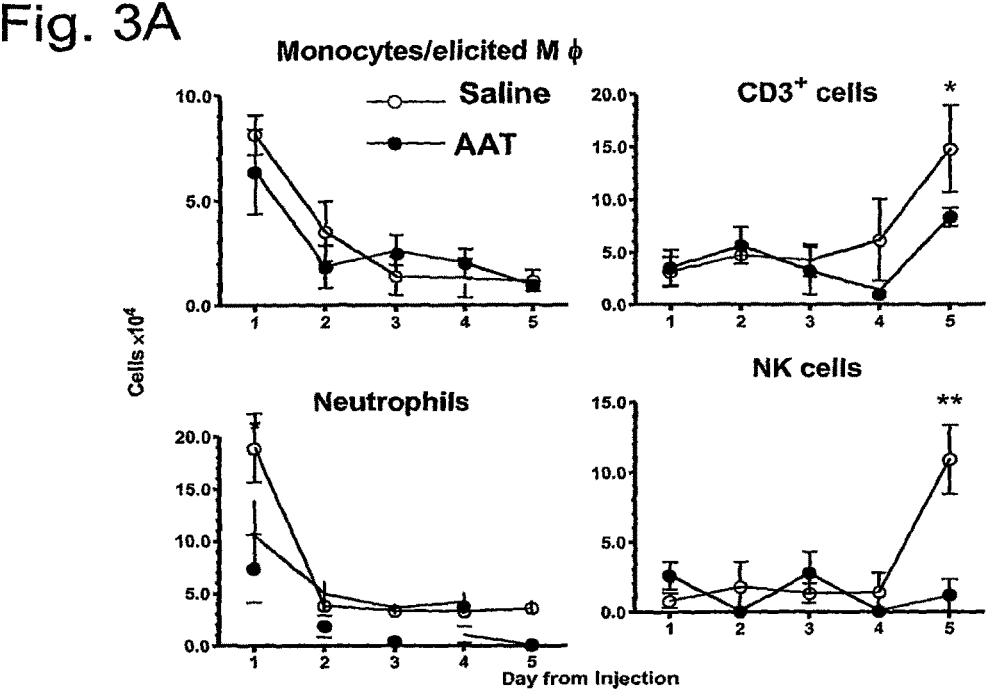
FIGS. 3A-3C illustrate an exemplary method of the effect of AAT on MHC-incompatible, NIH-3T3-fibroblast-elicited peritoneal cellular infiltrates. (A) Cell numbers. The number of cells in each subpopulation was calculated from the percentages obtained by FACS analysis, and total number of cells in the infiltrate. (B) Representative FACS analysis. (C) Effect of AAT on intensity and function of infiltrate elicited by islet allograft. Left, Hematoxylin and Eosin (H&E) staining of day 7 islet allografts. Right, Immunohistochemistry (IHC) with anti-insulin antibodies of day 15 islet grafts. R, renal parenchyma, G, graft, C, renal capsule.
Figure 3B:
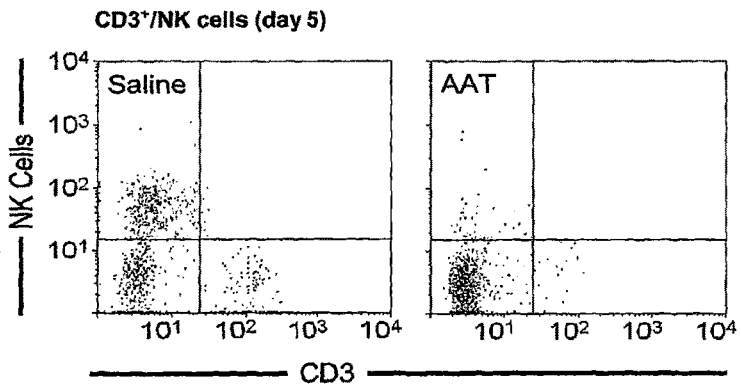
Figure 3C:
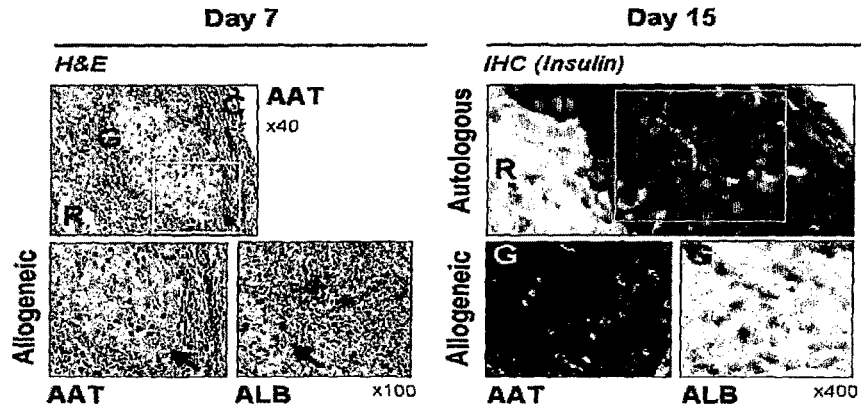

FIGS. 3A-3C illustrate an exemplary method of the effect of AAT on MHC-incompatible, NIH-3T3-fibroblast-elicited peritoneal cellular infiltrates. Mice (C57BL/6; H-2b) were injected i.p. 0.1 ml saline or AAT (1 mg) followed by 1 ml NIH-3T3 cells (1'107 cells in saline; H-2d). Peritoneal lavage was performed daily on days 1-5 and cell subpopulations were identified by FACS analysis. (n=3 per treatment). (A) Cell numbers. The number of cells in each subpopulation was calculated from the percentages obtained by FACS analysis, and total number of cells in the infiltrate.* P<0.05, ** P<0.01 between cell numbers on the same day. (B) Representative FACS analysis. (C) Effect of AAT on intensity and function of infiltrate elicited by islet allograft. Left, Hematoxylin and Eosin (H&E) staining of day 7 islet allografts. A section of AAT-treated islet graft (white frame) is compared to a similar section of ALB-treated diabetic recipient mouse (full treatment protocol, see FIG. 1A). Arrow points at border between islet and surrounding infiltrate. Right, Immunohistochemistry (IHC) with anti-insulin antibodies of day 15 islet grafts. A section of autologous islet graft (white frame) is compared to similar sections of allografts of AAT- and ALB-treated recipient mice. R, renal parenchyma, G, graft, C, renal capsule.

As illustrated in FIG. 3A, introduction of allogeneic cells evoked a cellular infiltrate that consisted of early appearing neutrophils and activated macrophages, and late appearing CD3+ and NK cells (FIG. 3B). AAT-treated mice exhibited a reduction in neutrophils, CD3+ and NK cells, dark color is insulin staining.

To evaluate the level of cellular infiltration into grafted islets, grafts from AAT- and ALB-treated recipient mice were removed on day 7, fixed in paraformaldehyde and stained with Hematoxylin and Eosin. As depicted in FIG. 3C (left), a cellular infiltrate is demonstrable regardless of AAT treatment, and includes neutrophils and lymphocytes. However, the infiltrates evoked by grafts of ALB-treated recipient mice were more massive and caused the disruption of islet borders, compared to intact islets of AAT-treated recipient mice. To evaluate islet function, grafts from AAT- and ALB-treated recipient mice were removed on day 15, and immunohistochemistry was performed with anti-insulin antibodies, dark color is insulin staining. As depicted in FIG. 3C (right), insulin production is preserved on day 15 in islets of AAT-treated recipients.

Example 4

FIGS. 4A-4H illustrate an exemplary method of the effect of AAT on islet responses. (A-D) Islets from C57BL/6 mice were cultured at 100 islets/well, in duplicate. AAT was incubated at the indicated concentrations for 1 hour before the addition of IFNγ (5 ng/ml) plus IL-1β (10 ng/ml). 72 hours later, supernatants were collected and islet viability was assessed. Islet cells responses in the absence of AAT were set at 100%. Data are combined from 3 individual experiments, in duplicate. $P<0.01$, * $P<0.001$ between AAT-treated and untreated islets. Mean±SEM of a. nitrite levels, b. Cell viability and c. MIP-1α levels. Dashed line represents islets incubated at one-30th the concentration of IFNγ/IL-1β. d. TNFα levels. (E) Insulin induction assay. Islets were incubated in triplicate (20 islets/well) in the presence of AAT (0.5 mg/ml) or ALB (0.5 mg/ml) 1 hour before addition of IFNγ (5 ng/ml) plus IL-1β (10 ng/ml). 24 hours later, islets were transferred to a 3 mM or 20 mM glucose solution for 30 minutes and insulin levels were measured. Vertical axis depicts the ratio between insulin levels at both glucose concentrations.* $P<0.05$ between AAT-treated and ALB-treated islets. (F) Streptozotocin toxicity. C57BL/6 mice were injected i.p. with AAT (5 mg) or saline, one day before, on same day and one day after injection of streptozotocin (225 mg/kg) or saline (n=3 per group). 48 hours later, pancreata were removed and insulin-containing cells were identified by immunohistochemistry. Each image depicts a representative islet from one pancreas. Graph, mean±SEM percent change of insulin-containing cells as determined manually from images of 2 islets per pancreas (n=6 per treatment group).* $P<0.05$. (G) Cellular content of islets. Freshly isolated islets (100 islets in triplicate) and residual non-islet pancreatic debris were dissociated into single cell suspensions and stained for FACS analysis with anti-CD45-APC or isotype control antibody. Shaded area, islets. Open area, debris. (H) MHC class II expression. Islets from C57BL/6 mice were cultured (100 islets/well in duplicate) in the presence of AAT (0.5 mg/ml) 1 hour before the addition of IFNγ (5 ng/ml) plus IL-1β (10 ng/ml). 24 hours later, islets were dissociated into single cell suspensions and double-stained for FACS analysis with anti-CD45-APC and anti-MHCII-PE, or isotype control antibodies. Left, Mean±SEM percent change from control (CT) unstimulated islets. * $P<0.05$ between AAT-treated and untreated islets. Right, Representative FACS analysis; Shaded area, AAT-treated islets. Open area, stimulated islets. Events are gated for CD45+.

AAT Modifies Islet Response to Proinflammatory Mediators

Figure 4A:
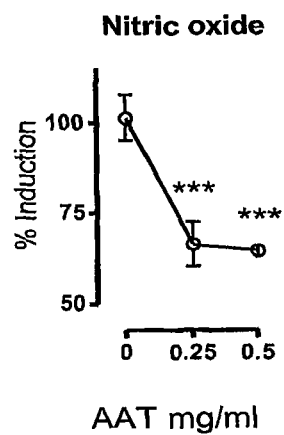
FIGS. 4A-4H illustrate an exemplary method of the effect of AAT on islet responses. (A-D) Mean±SEM of A. nitric levels, B. Cell viability and C. MIP-1α levels. Dashed line represents islets incubated at one-30th the concentration of IFNγ/IL-1β. D. TNFα levels. (E) Insulin induction assay. (F) Streptozotocin toxicity. Each image depicts a representative islet from one pancreas. (G) Cellular content of islets. (H) MHC class II expression.
Figure 4B:
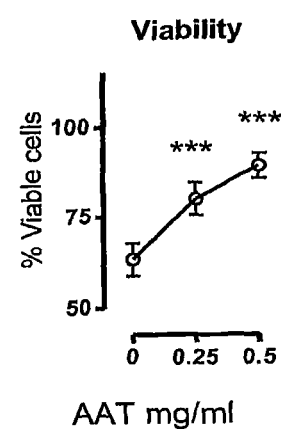
Figure 4C:
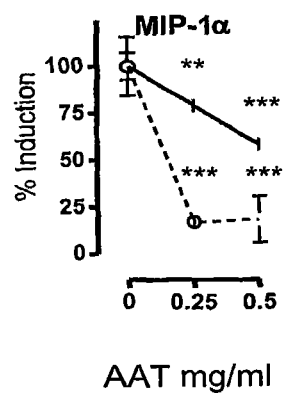
Figure 4D:
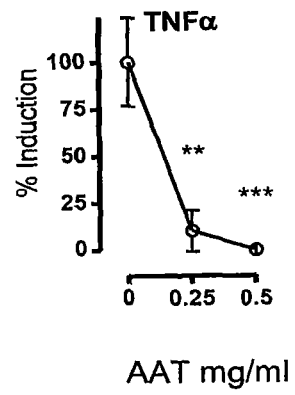
Figure 4E:
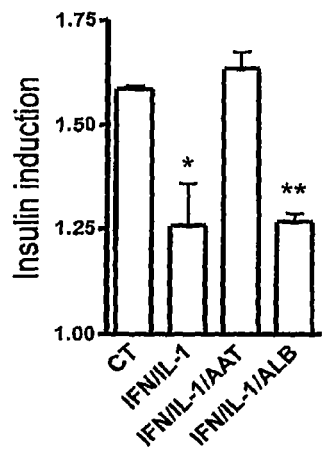
Figure 4F:
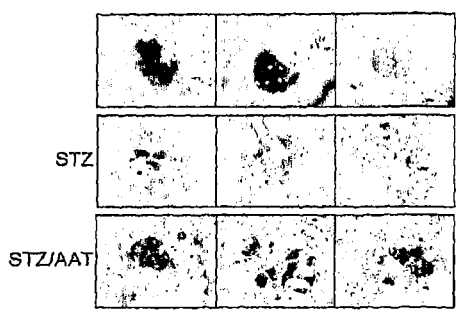
Figure 4G:
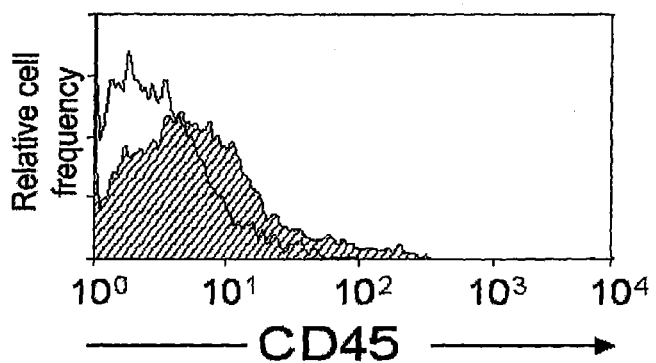
Figure 4H:
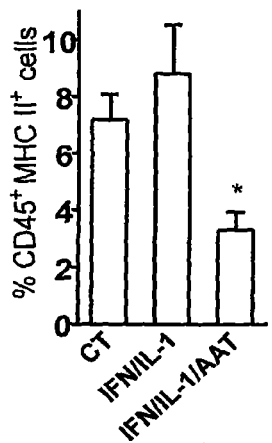
Figure 4H:
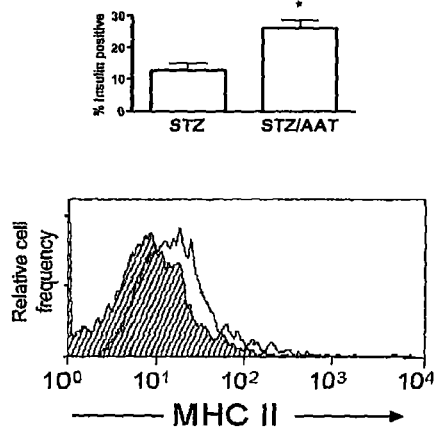

Various islet responses to IL-1β/IFNγ were examined in vitro. Islets exposed to IL-1β/IFNγ for 72 hours produce nitric oxide (NO) in a concentration-dependent manner and exhibit NO-dependent loss of viability. As shown in FIGS. 4A and B, in the presence of AAT, less NO was produced and greater islet viability was obtained. The production of MIP-1α was decreased in the presence of AAT, particularly when stimulated by low concentrations of IL-1β/IFNγ (FIG. 4C). Notably, TNFα level in supernatants was markedly diminished by AAT (FIG. 4D). Insulin induction was inhibited by IL-1β/IFNγ, but was intact in the presence of IL-1β/IFNγ plus AAT (FIG. 4E). To test the effect of AAT on islets in vivo, STZ toxicity was evaluated. AAT (2 mg) was administered one day before, on the same day and a day after STZ injection. Immunohistochemistry of pancreata with anti-insulin antibodies at 48 hours after STZ injection reveals more insulin-producing cells in islets of AAT- than ALB-treated mice (26.3%±2.6 and 12.8%±2.3 insulin-producing cells per islet, respectively, FIG. 4f). White cell content of freshly isolated islets was evaluated by FACS analysis. Islets contain CD45+ cells (FIG. 4G) that are also positive for the monocytic/granulocytic markers GR1 and F4/80 (data not shown). This cell population responded to AAT with decreased surface MHC class II (FIG. 4H).

Example 5

FIGS. 5A-5D illustrate the effect of AAT on TNFα. (A) Islets from C57BL/6 mice were cultured (100 islets/well in triplicate) in the presence of AAT (0.5 mg/ml) or TACE inhibitor (10 mM) 1 hour before stimulation by IFNγ (5 ng/ml) plus IL-1β (10 ng/ml). Left, mean±SEM change in TNFα, in supernatants after 72 hours of incubation. Right, mean±SEM fold change in membrane TNFα on islet cells after 5 hours of incubation, according to FACS analysis.*** $P<0.001$ compared control (CT) levels in the absence of AAT. (B) Representative FACS analysis of membrane TNFα on stimulated islet cells in the absence (open area) or presence (shaded area) of AAT. Events are gated for CD45+. (C) Streptozotocin-induced hyperglycemia. C57BL/6 mice were injected i.p. with saline (n=3), AAT (5 mg, n=3) or TNFα (1 mg/kg, n=3) or administered p.o. with TACE inhibitor (TACEi, 60 mg/kg, n=6) one day before injection of STZ (225 mg/kg, i.p.). Subsequently, AAT and TNFα were injected daily; TACE inhibitor was administered twice a day. At 48 hours, mean±SEM glucose levels are compared to those of normal littermates (n=3). * $P<0.05$, ** $P<0.01$ compared to saline-treated, STZ-injected mice.

AAT Inhibits Release of Membrane TNFα.

Figure 5A:
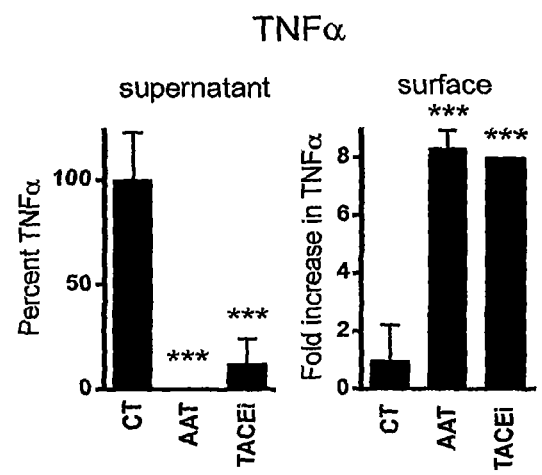
FIGS. 5A-5D illustrate the effect of AAT on TNFα. (A) Islets from C57BL/6 mice were cultured (100 islets/well in triplicate) in the presence of AAT (0.5 mg/ml) or TACE inhibitor (10 mM) 1 hour before stimulation by IFNγ (5 ng/ml) plus IL-1β (10 ng/ml). Left, mean±SEM change in TNFα, in supernatants after 72 hours of incubation. Right, mean±SEM fold change in membrane TNFα on islet cells after 5 hours of incubation, according to FACS analysis. (B) Representative FACS analysis of membrane TNFα on stimulated islet cells in the absence (open area) or presence (shaded area) of AAT. (C) Streptozotocin-induced hyperglycemia.
Figure 5B:
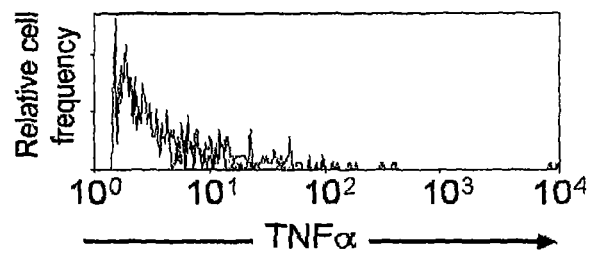

Proteolytic cleavage of membrane TNFα releases soluble TNFα from activated cells by the action of TNFα-converting-enzyme (TACE). The inventors examined the levels of membrane TNFα on stimulated islets in the presence of AAT. The effect of AAT was compared to that of a TACE inhibitor. Both AAT and TACE inhibitor decreased TNFα levels in supernatants of islets exposed to IL-1β/IFNγ (FIG. 5A, left). Under these conditions, membrane TNFα accumulated on the cell surface of CD45+ islet cells (FIG. 5A, right).

Figure 5C:
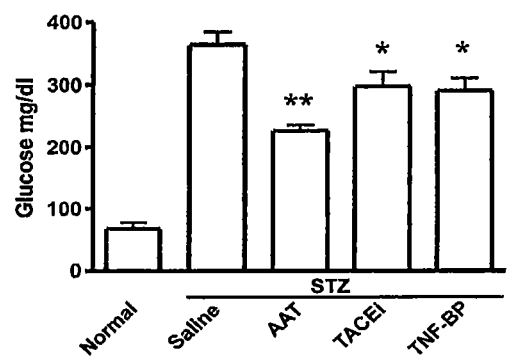

To assess the possibility that islet protection occurs via inhibition of release of membrane TNFα in vivo, TACE inhibitor, p75 TNF receptor (TNF BP) or AAT were introduced to mice prior to STZ injection. Although all mice developed hyperglycemia after day 4, the progression of β-cell toxicity was significantly affected by treatments. As shown in FIG. 5C, the effect of STZ at 48 hours was decreased in the presence of AAT (a decrease of 23.2%±2.3 in fasting glucose levels compared to STZ/saline injected mice). The effect of TACE inhibitor and p75 TNF receptor was not as profound. Similarly, TACE inhibitor prolonged islet graft survival to a lesser extent than AAT (preliminary data not shown).

Figure 5D:
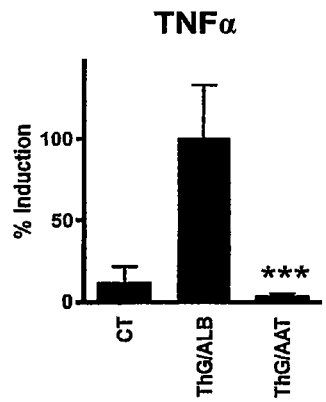
Figure 6A:
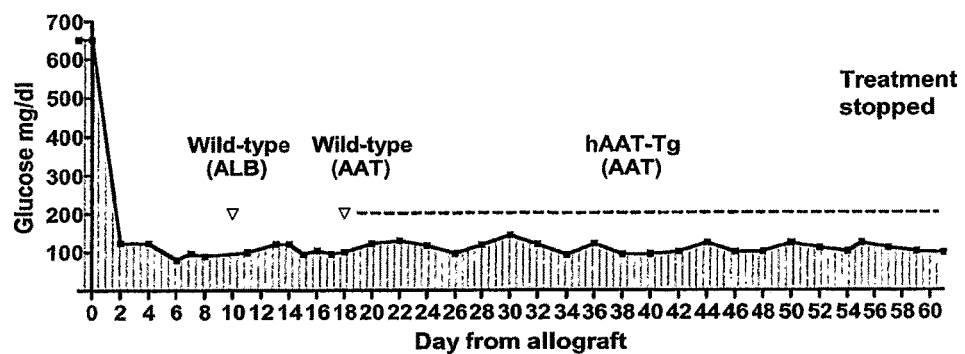
FIGS. 6A-6D illustrate the effect of AAT on Islet allograft transplantation. 6A illustrates the time course study after transplantation. 6B illustrates an immune infiltrate found outside the graft area. 6C illustrates an increase in the presence of CD4+ and a comparative decrease in monocytes and neutrophils. 6D illustrates levels of glucose reflecting a level of tolerance with respect to days following allografting of the same donor (left) and a 3rd donor re-graft (right), indicating induction of specific immune tolerance.
Figure 6B:
Figure 6C:
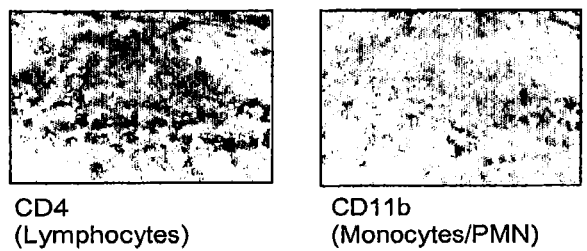
Figure 6D:
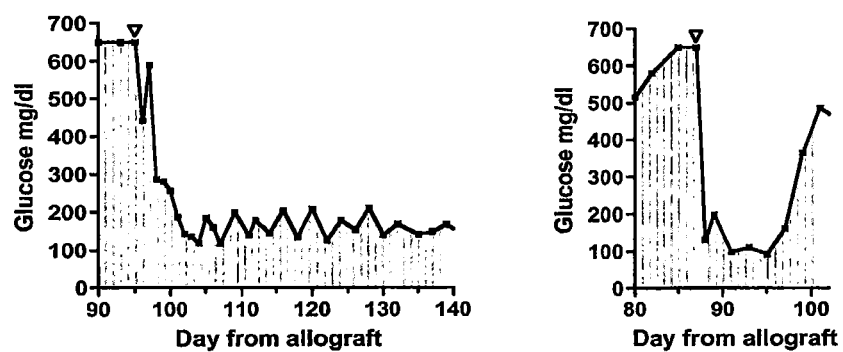
Figure 7A:
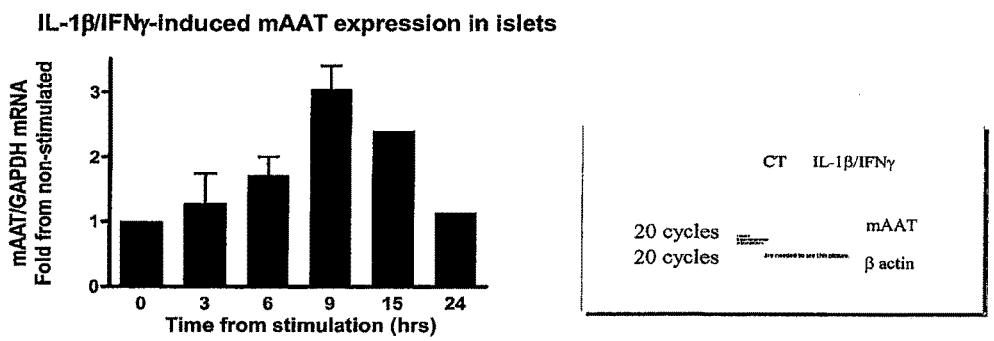
FIGS. 7A-7E illustrate the production of AAT by islet cell and reflection of islet graft survival. 7 A illustrates a time course expression of mouse AAT mRNA after cytokine production (IL-1β and IFNγ) (left) and at 8 hours (right). 7B illustrates an example of islet injury during pancreatitis; the histology of normal islets (top left), the histology of islets of an inflamed pancreas (top right) and expression of mouse AAT in islets obtained from the pancreata in an acute pancreatitis model (bottom). 7C illustrates an example of samples of islet allografts taken post grafting and the percent change in AAT mRNA levels were assessed. 7D illustrates an example of islet protection from cytokine injury with endogenous AAT by introducing oncostatin M (an interleukin 6 (IL-6) family member) that induces AAT expression in islets, oncostatin M and AAT levels (top left); nitric oxide and viability levels assessed (top right) and nitric oxide production representing islet viability after 4 day exposure to oncostatin M and AAT production decreasing cytokine effects on the islets (bottom).
Figure 7B:
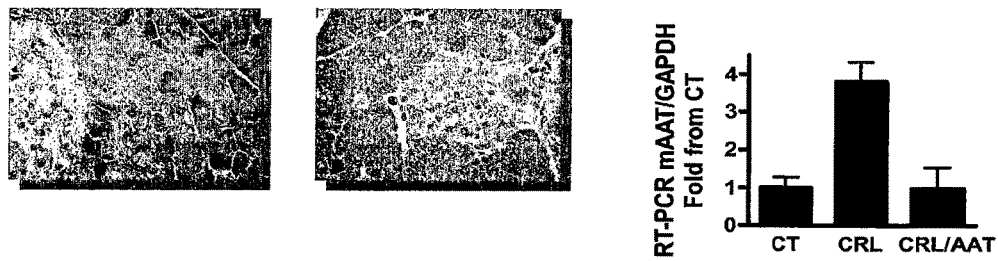
Figure 7C:
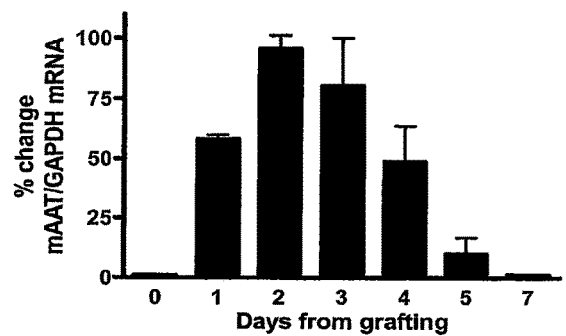
Figure 7D:
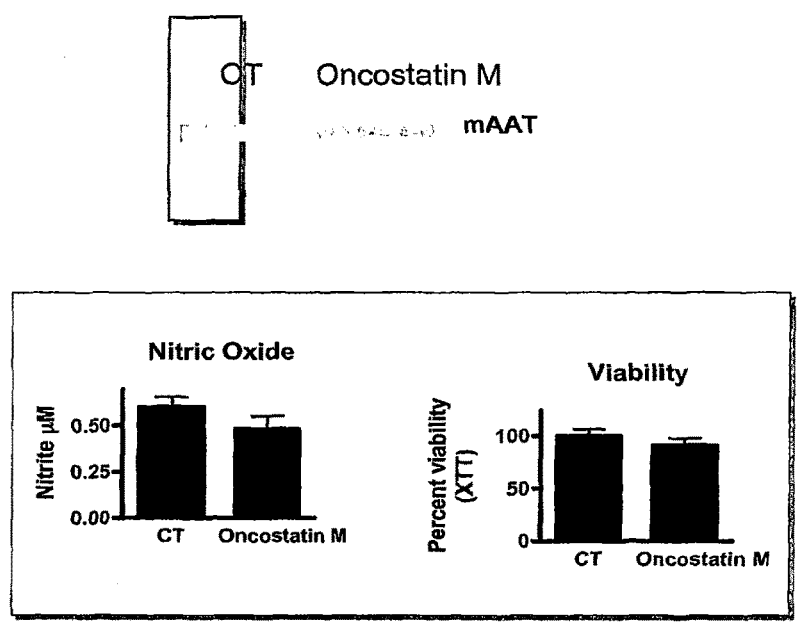
Figure 7E:
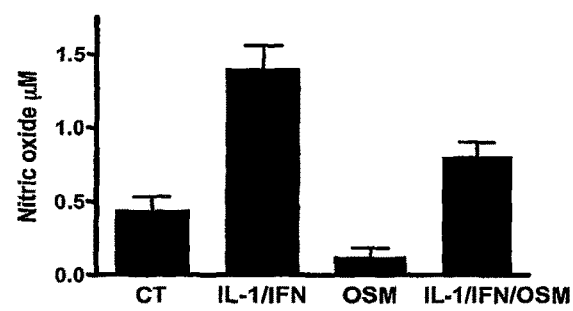
Figure 8A:
FIGS. 8A-8D illustrate the effect of AAT on human islets and the production of nitric oxide (8A), TNF-α production (8B), IL-6 (8C) and IL-8 (8D).
Figure 8B:
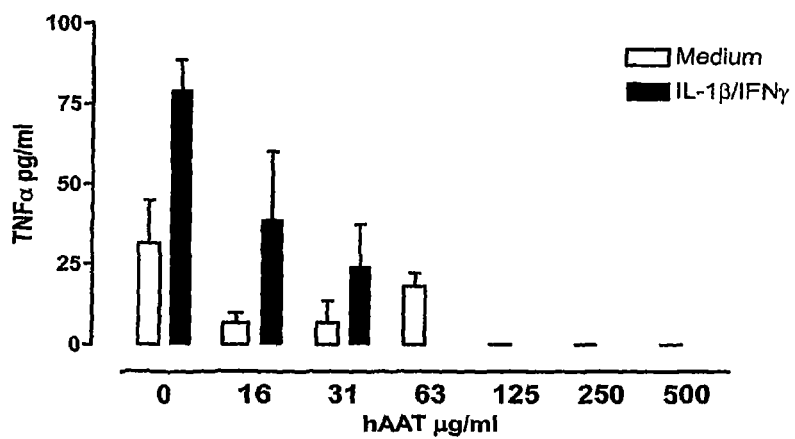
Figure 8C:
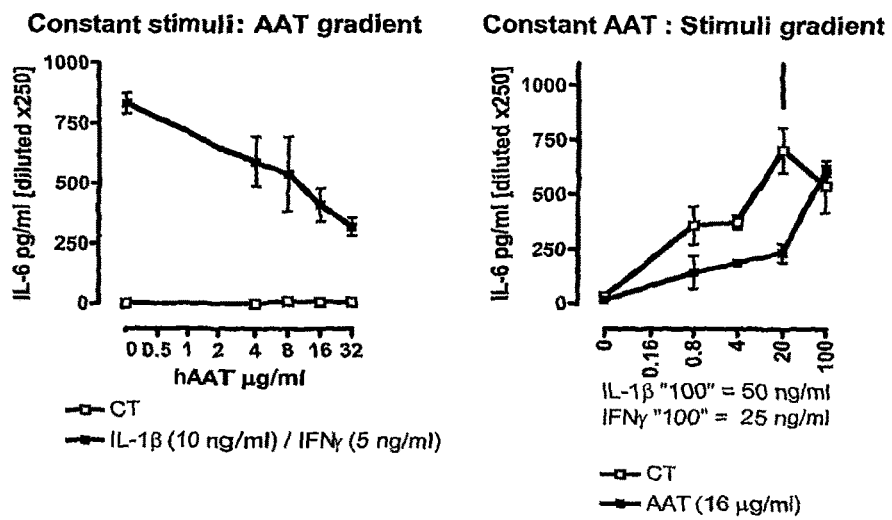
Figure 8D:
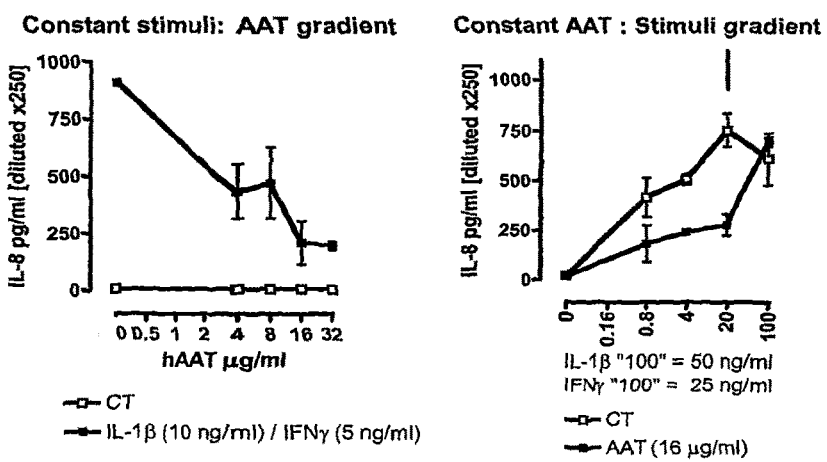

Splenocytes that were harvested 48 hours after ThG injection produced TNFα in culture (FIG. 5D). AAT administered prior to thioglycolate decreased TNFα release from cultured splenocytes. A similar trend was found with IFNγ (data not shown), signifying that the response to ThG had effects that extend beyond the peritoneal compartment and that pretreatment with AAT reduced these effects.

Example 6

FIGS. 6A-6D illustrate the effect of AAT on Islet allograft transplantation. 6A illustrates the time course study after transplantation of islet cells. This example indicates that treated mice maintain normoglycemia over a 60 day period (n=4), after the AAT therapy was withdrawn. After withdraw of the therapy, the normoglycemia lasted another 20 days. 6A illustrates the glucose follow-up. Positive insulin staining in a day −85 treated islet graft was also demonstrated (data not shown). 6B illustrates an immune infiltrate found outside the graft area. 6C illustrates an increase in the presence of CD4+ and a comparative decrease in monocytes and neutrophils. It was also shown that massive vascularization was evident inside the graft (data not shown). It has been observed that long-lasting accepted islet grafts can be spared from an immune alloresponse even after therapy removal, whether the therapy had evoked an immune tolerance specific for the strain of donor islets was evaluated. For this, grafts were explanted by nephrectomy and the now-hyperglycemic original recipients were re-transplanted with either the same strain of islets as before (n=2), or a 3rd strain which they had never encountered before (n=2). In accordance with established strain specific immune tolerance, mice accepted grafts from original donors, but had acutely rejected 3rd-strain grafts (6D); the same donor (left) and a 3rd donor re-graft (right).

Example 7

FIGS. 7A-7E illustrate the production of AAT by islet cell and reflection of islet graft survival. 7A illustrates a time-course expression of mouse AAT mRNA after cytokine production (IL-1β and IFNγ) (left) and at 8 hours (right). To demonstrate the relevance of endogenous alpha-1-antitrypsin in physiological conditions, the issue of islet injury during pancreatitis was addressed. In mouse model of acute pancreatitis, isolated islets of pancreata that are inflamed express inducible alpha-1-antitrypsin. 7B illustrates an example of islet injury during pancreatitis; the histology of normal islets (top left), the histology of islets of an inflamed pancreas (top right) and expression of mouse AAT in islets obtained from the pancreata in an acute pancreatitis model (bottom). Alpha-1-antitrypsin levels during pancreatitis (caerulein model for acute pancreatitis). Top, histology of an islet in a normal pancreas (left) and an islet in an inflamed pancreas (right), representative of n=3. Bottom, expression of mouse alpha-1-antitrypsin in islets obtained from pancreata in acute pancreatitis model. Treatment of mice with exogenous alpha-1-antitrypsin resulted in downregulation of endogenous alpha-1-antitrypsin expression, as well as decrease in serum TNFα levels (not shown).

To demonstrate the relevance of endogenous alpha-1-antitrypsin in islet transplantation, islet allografts from untreated transplanted mice on days 1 through 7 after transplantation (n=3) were excised. These were examined for alpha-1-antitrypsin expression and reveal a pattern which may fit inflammation phase (days 1-3) followed by loss of islet mass (days 4-7). 7C illustrates an example of samples of islet allografts taken post grafting and percent change in AAT mRNA levels were also assessed. Total RNA was extracted and mRNA for alpha-1-antitrypsin evaluated by RT-PCR.

Islet protection from cytokine injury was examined using endogenous alpha-1-antitrypsin by introducing oncostatin M, a member of IL-6 family that induces alpha-1-antitrypsin expression in islets without causing islet death. After 4 days that human islets were incubated with oncostatin M, for the purpose of accumulation of sufficient alpha-1-antitrypsin, islets were added the β-cell-toxic combination of IL-1β/IFNγ. Pretreated islets that had excess alpha-1-antitrypsin were protected from injury, supporting the concept that islet-derived alpha-1-antitrypsin may participate in islet protection during inflammation. 7D illustrates an example of islet protection from cytokine injury with endogenous AAT by introducing oncostatin M (an interleukin 6 (IL-6) family member) that induces AAT expression in islets, oncostatin M and AAT levels (top left); nitric oxide and viability levels assessed (top right). Bottom, human islets exposed to oncostatin M for 4 days produce enough alpha-1-antitrypsin to diminish the effects of IL-1β/IFNγ added for an additional 48 hours.

Example 8

In one exemplary study, alpha-1-antitrypsin on human islets was examined. FIGS. 8A-8D illustrate the effect of AAT on human islets. The production of nitric oxide (8A), TNFα production (8B), IL-6 (8C) and IL-8 (8D) was examined. 100 human islets per well were seeded in triplicates and added alpha-1-antitrypsin (AAT) 2 hours before stimuli. Supernatants were assayed 72 hours later. 3A, nitric oxide; 3B, TNFα; 3C, IL-6; 3D, IL-8. Results are mean±SEM and are representative of separate islet isolations from three human donors.

Methods

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R.I. Freshney, ed., 1986).

Mice. C57BL/6 and DBA/2 females were purchased from Jackson Laboratories.

Induction of hyperglycemia by streptozotocin, islet isolation and islet transplantation. In one exemplary method, 5-6 weeks old C57BL/6 mice were treated intraperitoneally (i.p.) with 225 mg/kg Streptozotocin (STZ) (Sigma). Mice with established hyperglycemia were used at least 5 days after STZ administration. Islets were isolated from DBA/2 mice on day of transplantation, or 24 hours before in vitro assays, by enzymatic digestion of pancreata, by means known in the art, with minor modifications. Briefly, mice were anesthetized with i.p. ketamine (50 mg/kg, Vedco Inc.) and xylazine (10 mg/kg, Vedco Inc.). Each pancreas was inflated with 3.5 ml cold collagenase (1 mg/ml, type XI, Sigma), excised and immersed for 40 minutes at 37° C. in water bath. Pancreata were gently vortexed and filtered through 500-micron metal sieve. The pellet was washed twice in cold HBSS containing 0.5% BSA (Sigma) and reconstituted in RPMI-1640 (Cellgro, Mediatech) supplemented with 10% FCS (Cellgro), 50 IU/ml Penicillin (Cellgro) and 50 µg/ml streptomycin (Cellgro). Islets were collected on a 100-micron nylon cell strainer (BD Falcon), released into a petri dish by rinsing with HBSS (Cellgro, Mediatech) and 0.5% BSA (Sigma) and hand-picked under a stereomicroscope. For transplantation, 450 islets were thoroughly washed from residual FCS in HBSS and 0.5% BSA and mounted on 0.2 ml tip for immediate transplantation. For in vitro assays islets were left to incubate for 24 hours at 37° C. Islet transplantation was performed into the left renal subcapsular space. Recipient mice were anesthetized, as described above. An abdominal wall incision was made over the left kidney. Islets were released into the subcapsular space through a puncture and the opening was sealed by means known in the art. Blood glucose follow-up was performed 3 times a week from end-tail blood drop using glucosticks (Roche). (Nanji, S. A. & Shapiro, A. M. Islet transplantation in patients with diabetes mellitus: choice of immunosuppression. BioDrugs 18, 315-28 (2004).)

Development of anti-human-AAT antibodies in mice. In another exemplary method, in order to evoke specific antibody production against human AAT, mice were injected i.p. with 10 mg human AAT per 20-gram mouse for four times in intervals of 1 week. Mice were used in experiments 2 months after last administration. Antibody production was evaluated before transplantation experiments were carried out.

In one example, assaying for anti-human-AAT antibody levels was performed as described in the art. Briefly, mouse sera were kept at −70° C. until assayed for anti-human AAT levels. Plates were coated with human AAT or albumin (2 µg/ml) in PBS at 4° C. overnight, then washed and blocked for 1 hour at 25° C. as described. Negative control serum was used in addition to test serum. Bound anti-AAT antibody using standard TMB substrate solution was measured (Sigma).

Cells. NIH-3T3 cell line (e.g. ATCC) were cultured. On day of peritoneal inoculation, $1 \times 10^7$ cells were freshly collected by trypsinization and washed with cold PBS. Pellet was resuspended in 1 ml cold PBS for immediate injection.

Infiltration experiments. Peritoneal infiltration was elicited by i.p. injection of 1 ml autoclaved thioglycolate (3% w/v, Sigma) or allogeneic cells (NIH-3T3), together with 0.1 ml saline, human albumin, human AAT or oxidized AAT. Peritoneal lavage was performed at 24 and 48 hours (thioglycolate) or on days 1-5 (allogeneic cells). For lavage, mice were anesthetized by isoflurane inhalation and injected immediately with 5.5 ml cold PBS containing 5% FCS and 5 U/ml heparin into the peritoneal cavity. After massaging the abdomen, peritoneal fluid was recovered. Red blood cells were lysed (RBC lysing buffer, BD PharMingen) and cell counts were performed with a hemocytometer. Cells were then isolated. Cells (about $1 \times 10^6$/polypropylene vial) were incubated with FcγRIII/11 receptor block antibodies (Table I) for 10 min. Cells were then divided into two groups and incubated with mAbs for leukocytes and either CD3/NK cells or neutrophil/monocytes/macrophages (Table I) for 30 min. Cells were washed and fixed. The number of cells expressing a particular marker was calculated by multiplying percentages obtained from flow-cytometry by the concentration of cells in lavage fluid.

TABLE I

Rat Anti-Mouse mAbs Used for Flow Cytometry

| Purpose | mAb | (1) Specificity | (2) Source |
|---|---|---|---|
| Blocking | 2.4G2 | FcγRIII/II | BD PharMingen |
| Leukocytes | 30-F11 (APC) | CD45 (leukocytes) | BD PharMingen |
| Macrophages and | F4/80 (PE) | F4/80 (macrophages/monocytes) | eBiosciences |
| Neutrophils | RB6-8C5 (FITC) | GR1 (neutrophils/monocytes) | BD PharMingen |
| CD3 | DX5 (PE) | Pan-NK cells | Miltenyi Biotec |
| NK cells | 17A2 (FITC) | CD3 | BD PharMingen |
| TNFα | MP6-XT22 (PE) | Mouse TNFα | eBiosciences |
| MHC class II | M5/114.15.2 (PE) | I-A$^{b/d}$, I-E$^d$ | BD PharMingen |
| Isotype control | Rat IgG1 (PE) | | eBiosciences |

An insulin assay and immunohistochemistry were performed by means known in the art (Nanji, S. A. & Shapiro, A.M. Islet transplantation in patients with diabetes mellitus: choice of immunosuppression. BioDrugs 18, 315-28 (2004)).

AAT Oxidation by Myeloperoxidase (MPO) System.

In one example, AAT (4 mg/ml) was incubated at 37° C. for 45 minutes with MPO (1 U/ml, Sigma), $H_2O_2$ (80 µM, Sigma) and NaCl (2.5 mM) in PBS, pH 7.4, by means known in the art. Reaction was terminated by boiling for 1 hour followed by filter-centrifugation of the system products. In this example, boiling was needed for the inactivation of MPO but this did not inactivate AAT (data not shown). Loss of activity of oxidized AAT was confirmed by elastase activity assay.

Elastase Activity Assay.

In another exemplary method, inhibition of a the serine protease elastase was evaluated 30 minutes after co-incubation of AAT or oxidized AAT with porcine elastase (Sigma) in triplicate, by known methods. The ability of elastase to liberate 4-nitroaniline ($A_{410}$) from SucAla$_3$-PNA was determined by kinetic measurement of light absorbance at 410 nm. Activity in the absence of inhibitors was set as 100% at the linear range of the assay.

Cytokine assays. An electrochemiluminescence (ECL) assay as known in the art was used for the measurement of mouse TNFα and MIP-1α. Briefly, cytokine-specific goat anti-mouse affinity purified antibodies were labeled with ruthenium (e.g. BioVeris) according to manufacturer's instructions. Biotinylated polyclonal anti-mouse antibodies (e.g. R&D Systems) were used. The amount of TNFα and MIP-1α chemiluminescence was determined using an Origen Analyzer (BioVeris).

Membrane TNFα.

Membrane TNFα on islet cells was detected by modification of a method for the evaluation of membrane TNFα on human PBMC. Briefly, single-cell suspension of islets was incubated with anti-mTNFα-PE mAb (Table I). Cells were washed with FACS buffer and resuspended in 0.5 ml 2% EM-grade formaldehyde.

Nitric Oxide Assay.

Nitrite levels in supernatants were determined using Griess reagent (Promega), as previously described (Chan, E. D. & Riches, D. W. Am 1 Physiol Cell Physiol 280, C441-50 (2001)).

Apoptosis Assay.

The protective effect of AAT on islets may address one of the major obstacles in islet transplantation today, namely the inadequacy of islet mass and post-isolation islet viability. Freshly isolated human islets activate stress signaling pathways and exhibit high rate of apoptosis due to the process of isolation, necessitating the use of more than one islet donor per diabetic patient (Nanji, (2004); Abdelli, S. et al. Intracellular stress signaling pathways activated during human islet preparation and following acute cytokine exposure. Diabetes 53, 2815-23 (2004)).

In this example, apoptosis that follows islet isolation is diminished when islets are cultured with AAT (data not shown) and demonstrate that islets that are cultured with AAT for 24 hours prior to transplantation are able to normalize serum glucose levels of diabetic mice when transplanted autologously at an otherwise sub-functional mass (data not shown).

AAT Dosage.

Normal human plasma contains 0.8-2.4 mg/ml AAT, with a half-life of 5-6 days. In gene transfer studies in C57BL/6 mice, plasma levels of 0.8-1.0 mg/ml were achieved and provided protection from type I diabetes in NOD mice (Song, S. et al Gene Therapy 11, 181-6 (2004)). AAT administered intraperitoneally at 0.3-1.0 mg per mouse protected from TNFα-induced lethal response, and 0.8 mg AAT protected from D-galactosamine/LPS induced hepatic injury. Libert, C., et al., J Immunol 157, 5126-9 (1996).

Since AAT levels rise 3- to 4-fold during the acute phase response 1, 2 mg per mouse results in plasma levels that do not exceed physiological levels.

Statistical Analysis.

Comparisons between groups were analyzed by two-sided t-test or ANOVA for experiments with more than two subgroups. Results are presented as mean±SEM.

Prolongation of Islet Graft Survival by AAT.

In the present study, administration of clinical grade AAT to mice transplanted with allogeneic islets prolonged graft survival. In addition, AAT reduced migration of neutrophils and the subsequent infiltration of lymphocytes and NK cells in models of peritonitis. AAT also decreased secretion of TNFα and MIP-la from islets and inhibited surface MHC class II expression on CD45+ islet cells in vitro. AAT was protective in a model of streptozotocin (STZ)-induced β-cell toxicity. Thus, it appears that AAT monotherapy targets several aspects of an activated inflammatory immune system, culminating in prolongation of islet allograft survival.

Effect of AAT on Cell Infiltration.

AAT diminished neutrophil migration into the peritoneum of mice injected with either thioglycolate or MHC-incompatible fibroblast cells. Other studies demonstrate that AAT inhibits neutrophil infiltration into kidneys during ischemia/reperfusion injury and into lungs following intratracheal administration of silica. In the present study AAT decreased islet production of MIP-la and TNFα, resulting in islets deficient in chemotactic capabilities and therefore less immunogenic. The detrimental effect of neutrophils recruited to islets has been clearly demonstrated.

The involvement of macrophages in islet destruction is critical; their presence precedes insulitis in NOD mice and in prediabetic BB rat, and their depletion is protective during islet transplantation in rats. Islets are potent recruiters of macrophages; of the 51 gene products identified in freshly isolated human islets by cDNA array, expression of MCP-1 was found to be high. In mice, blockade of MCP-1 prolongs islet allograft survival when combined with a short subtherapeutic course of rapamycin. Islet allograft rejection is associated with a steady increase in intragraft expression of MCP-2, MCP-5, CCL5, CXCL-10 and CXCL9, and the chemokine receptors CCR2, CCR5, CCR1 and CXCR337. Accordingly, CCR2−/− mice and CXCR3−/− mice exhibit prolongation of islet allograft survival. In transplant settings, cytokines that are produced locally, as TNFα and IL-1β, cause damage to proximal cells independent of antigen recognition, and complement activation is critical for graft survival independent of allospecific immunity. The relevance of macrophages during early events in islet graft rejection is strengthened by the identification of CD45, F4/80 and Grl positive cells that express MHC class II in freshly isolated islets. In the presence of AAT, MHC class II levels were decreased below those of IL-1β/IFNγ-stimulated and unstimulated islets, supporting the idea that the process of islet isolation is sufficient to provoke activation of inflammatory pathways in islet cells. In light of the involvement of neutrophils and macrophages in graft rejection, interference with their functions by AAT provides an unusually non-inflammatory environment for the survival and recovery of engrafted islets.

As shown in the present study and elsewhere intraperitoneal injection of allogeneic NIH-3T3 cells evokes infiltration of macrophage and neutrophil on days 1-2 and of CD3+ and NK cells on days 4-5. The intensity of the latter infiltration was decreased by administration of AAT prior to allogeneic cell-line injection, but not by administration of AAT on day 3 (data not shown). In transplant settings, early non-specific factors contribute to subsequent specific immune response. It is therefore possible that the decrease in CD3+ and NK cell infiltration in the present study is secondary to the functional failure of the early innate response. However, regardless of AAT treatment, histological examination of islet grafts demonstrated that the infiltrate evoked by allogeneic islets consists of neutrophils and lymphocytes. Nevertheless, day 7 infiltrate was diminished in AAT-treated recipients, and, according to day 15 insulin immunohistochemistry, the infiltrate caused less islet destruction. AAT inhibits release of TNFα.

Supernatants of IL-1β/IFNγ-stimulated islets contained strikingly less TNFα when incubated with AAT (induction of 100.0%±22.0 mean±SEM at 0 mg/ml AAT; 10.2%±11.2 at 0.5 mg/ml and 0.8%±0.1 at 1.0 mg/ml). In stimulated human PBMC, AAT was shown to diminish TNFα release without affecting TNFα-mRNA levels. In mice, accordingly, serum TNFα levels are decreased in LPS-injected AAT-treated mice. Importantly, treatment of mice with AAT blocks TNFα-mediated LPS-induced, but not TNFα-induced lethality in mice. In the present study, cultured mouse splenocytes isolated from thioglycolate-injected mice secreted less TNFα, 48 hours after injection of AAT.

In the presence of AAT, membrane TNFα accumulated in IL-1β/IFNγ-stimulated CD45+ islet cells. TNFα is released from the cell surface of macrophages by the action of TNFα converting enzyme (TACE), a metalloproteinase that cleaves membrane TNFα into the soluble form of TNFα. Inhibitors of TACE reduce TNFα release and increase the levels of membrane TNFα, as demonstrated by FACS analysis. Although the regulation of TACE activity is unclear, there is evidence to suggest that extracellular proteases are involved: TACE does not require its cytoplasmic domain for its activation, its activity does not depend on the amount of TACE on the cell surface, co-expression of TACE and transmembrane TNFα is not sufficient for processing of TNFα and the enzyme is expressed constitutively in various cells. Serpins, such as serpin PN-I52, are suggested to possess extracellular regulatory effects on various surface proteins.

TACE is likely to be relevant for graft rejection since TACE inhibitor decreased injury parameters in a rat model of post-transplant lung injury. In addition to a decrease in TNFα levels, the study shows lower expression of MCP-1 and ICAM-1, and a reduction in neutrophil infiltration. Similar findings were obtained with both AAT and a broad spectrum metalloproteinase inhibitor in a model of silica induced neutrophil influx into lungs. However, TACE inhibitor only partially reproduced the protective effect of AAT on islet graft survival (preliminary data). Similarly, AAT protection from STZ-induced hyperglycemia was only partially reproduced by TACE inhibition and by recombinant p75-TNF-receptor. Despite the fact that locally secreted TNFα is detrimental to islet graft function, there is, to our knowledge, no report that describes protection of islet grafts by neutralization of TNFα activity. This distinction between AAT and TACE inhibition supports the possibility that AAT affects multiple aspects of the immune system, including not only TNFα release but also events that are downstream to TNFα activities.

In one embodiment, it is contemplated that a composition of the present invention may include AAT, an analog thereof, a serine protease, TACE inhibitor (TACEi) or any combination thereof. These compositions may be administered to a subject having or in need of a transplant and or in need of immunotolerance therapy.

Transplanted Islets are Stimulated by the Process of Isolation.

The process of islet isolation initiates in the islets an inflammatory cascade of cytokines and chemokines. Thus, isolated islets contain an intrinsic proinflammatory potential that may affect local host immune responses. The mechanism of cytokine-induced islet toxicity is believed to involve expression of inducible nitric oxide synthase and subsequent production of nitric oxide (NO) by non-β-cells. In the present study, AAT decreased NO production in IL-1β/IFNγ-treated islets. Accordingly, islet viability was increased in a low NO environment, as attained by either incubation with a low concentration of stimulators (data not shown) or by introduction of AAT. Insulin induction, which is typically incomplete in the presence of cytokines, was intact in the presence of AAT and cytokines. In vivo, AAT protected islets in mice injected with STZ, as concluded by lower serum glucose levels. The portion of viable β-cells was visually assessed by insulin immunohistochemistry and was proportional to the decrease in serum glucose levels. The protection of AAT was limited to the initial days that follow STZ administration, suggesting that AAT interferes with NO production and immune activation and not with intracellular DNA alkylation. Freshly isolated non-stimulated CD45+ islet cells expressed MHC class II, which is involved in immune responses against islets. The levels of MHC class II were elevated in the presence of IL-1β/IFNγ and decreased in the presence of AAT. Interestingly, MHCII expression was unaffected by the presence of TACE (TNF alpha converting enzyme) inhibitor (data not shown), confirming that AAT activities extend beyond those of TACE inhibition.

According to the present study, the activities of AAT are directed against multiple components of the innate immune system, culminating in a protective effect on islet graft destruction. Islets in particular exhibited a high degree of protection from inflammatory processes in the presence of AAT. Pretreatment with AAT prior to islet transplantation may reduce both islet loss and the immunological response against the graft.

The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group and that other members of the described groups are included but may not be listed.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A method for reducing risk of onset of graft versus host disease (GvHD) in a human subject having a non-organ transplant and at risk of developing GvHD, comprising administering to the human subject a composition comprising alpha-1 antitrypsin (AAT) or a recombinant molecule thereof, and a pharmaceutically acceptable excipient, and reducing the risk of developing GvHD in the human subject.

2. The method of claim 1, further comprising administering one or more anti-rejection agent, anti-inflammatory agent, immunosuppressive agent, immunomodulatory agent, anti-microbial agent, anti-viral or combination thereof to the human subject.

3. The method of claim 1, wherein the GvHD is attributed to a stem cell or bone marrow implant in the human subject.

4. The method of claim 3, wherein the GvHD is attributed to bone marrow implantation and the human subject is administered the composition following the bone marrow implantation.

5. The method of claim 1, wherein the composition is administered to the human subject at a dose of about 0.1 mg/kg to about 100 mg/kg.

6. A method for reducing risk of onset of graft versus host disease (GvHD) in a non-organ transplant human subject, comprising, administering to the non-organ transplant human subject at risk of developing GvHD, a composition consisting essentially of alpha-1 antitrypsin (AAT) or recombinant molecule thereof, and a pharmaceutically acceptable excipient, to reduce the risk of developing GvHD in the human subject.

7. The method of claim 6, wherein the composition is administered after non-organ transplantation to reduce incidence of GvHD in the human subject as compared to a control human subject not receiving the composition.

8. The method of claim 1, wherein the AAT or the recombinant molecule thereof comprises a full-length AAT polypeptide and the AAT polypeptide is part of a fusion polypeptide.

9. The method of claim 8, wherein the fusion polypeptide comprises the full-length AAT polypeptide fused to an immunoglobulin constant region.

10. The method of claim 9, wherein the immunoglobulin constant region comprises an IgG1 constant region.

* * * * *

UNITED STATES PATENT AND TRADEMARK OFFICE
CERTIFICATE OF CORRECTION

PATENT NO. : 9,884,096 B2
APPLICATION NO. : 14/266535
DATED : February 6, 2018
INVENTOR(S) : Leland Shapiro et al.

Page 1 of 1

It is certified that error appears in the above-identified patent and that said Letters Patent is hereby corrected as shown below:

In Item (72) Inventors: delete "Shapiro Leland" and insert -- Leland Shapiro --

In Column 1, Line 15, insert -- FEDERALLY FUNDED RESEARCH
This invention was made with government support under grant numbers AI015614 and HL068743 awarded by National Institutes of Health. The government has certain rights in the invention. --

Signed and Sealed this
Eleventh Day of September, 2018

Andrei Iancu
*Director of the United States Patent and Trademark Office*